(12) United States Patent
Kawaguchi et al.

(10) Patent No.: US 7,456,217 B2
(45) Date of Patent: Nov. 25, 2008

(54) INHIBITORS OF ALPHA4 MEDIATED CELL ADHESION

(75) Inventors: Takayuki Kawaguchi, Tokyo (JP);
Sumihiro Nomura, Saitama (JP);
Mikiko Tsukimoto, Saitama (JP);
Toshiyuki Kume, Saitama (JP); Ila Sircar, San Diego, CA (US)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 182 days.

(21) Appl. No.: 11/179,729

(22) Filed: Jul. 13, 2005

(65) Prior Publication Data

US 2005/0282900 A1  Dec. 22, 2005

Related U.S. Application Data

(62) Division of application No. 10/333,985, filed as application No. PCT/US01/26594 on Aug. 27, 2001, now Pat. No. 7,026,501.

(60) Provisional application No. 60/229,128, filed on Aug. 31, 2000.

(51) Int. Cl.
A61K 31/195 (2006.01)
C07C 229/00 (2006.01)
(52) U.S. Cl. .......... 514/563; 514/539; 560/39; 562/450
(58) Field of Classification Search .......... 562/450; 560/39; 514/539, 563
See application file for complete search history.

(56) References Cited

U.S. PATENT DOCUMENTS

| 4,113,871 | A | 9/1978 | Stach et al. |
|---|---|---|---|
| 6,191,171 | B1 | 2/2001 | DeLaszlo et al. |
| 6,353,099 | B1 | 3/2002 | DeLazlo et al. |
| 6,420,418 | B1 | 7/2002 | Hagmann et al. |
| 6,469,047 | B1 | 10/2002 | Jackson et al. |
| 6,555,562 | B1 | 4/2003 | Archibald et al. |
| 2003/0166691 | A1 | 9/2003 | Archibald et al. |

FOREIGN PATENT DOCUMENTS

| GB | 2354440 A | 3/2001 |
|---|---|---|
| SU | 618038 | 9/1978 |
| WO | WO-95/12611 A1 | 5/1995 |
| WO | WO-95/26360 A1 | 10/1995 |
| WO | WO-96/22966 A1 | 8/1996 |
| WO | WO-96/33170 A1 | 10/1996 |
| WO | WO-98/53814 A1 | 12/1998 |
| WO | WO-98/53817 A1 | 12/1998 |
| WO | WO-98/53818 A1 | 12/1998 |
| WO | WO-98/54207 A1 | 12/1998 |
| WO | WO-98/58902 A1 | 12/1998 |
| WO | WO-99/06390 A1 | 2/1999 |
| WO | WO-99/06432 A1 | 2/1999 |
| WO | WO-99-06433 A1 | 2/1999 |
| WO | WO-99/06434 A1 | 2/1999 |
| WO | WO-99/06435 A1 | 2/1999 |
| WO | WO-99/06436 A1 | 2/1999 |
| WO | WO-99/06437 A1 | 2/1999 |
| WO | WO-99/10312 A1 | 3/1999 |
| WO | WO-99/10313 A1 | 3/1999 |
| WO | WO-99/26615 A1 | 6/1999 |
| WO | WO-99/26921 A1 | 6/1999 |
| WO | WO-99/26922 A1 | 6/1999 |
| WO | WO-99/35163 A1 | 7/1999 |
| WO | WO-99/36393 A | 7/1999 |
| WO | WO-99/37618 A1 | 7/1999 |
| WO | WO-99/43642 A1 | 9/1999 |
| WO | WO-99/48879 A1 | 9/1999 |
| WO | WO-99/06431 A1 | 11/1999 |
| WO | WO-99/61465 A1 | 12/1999 |
| WO | WO-99/64390 A1 | 12/1999 |
| WO | WO-99/64395 A1 | 12/1999 |
| WO | WO-99/67230 A1 | 12/1999 |
| WO | WO-00/37429 A2 | 6/2000 |
| WO | WO-02/18329 A1 | 3/2002 |

OTHER PUBLICATIONS

Hitesh N. Shroff et al., Bioorganic & Medicinal Chemistry Letters, vol. 6, No. 21, pp. 2495-2500, 1996.
Joanne L. Viney et al., The Journal of Immunol., vol. 157, 1996, pp. 2488-2497.
Michael J. Briskin et al., The Journal of Immunol., vol. 156, 1996, pp. 719-726.
Chemical Abstracts, vol. 65, No. 10, Abstract No. 15302d, 1966.
English translation of Office Action issued in Israeli Patent Application No. 154305, Dec. 2, 2007.

*Primary Examiner*—Taylor Victor Oh
(74) *Attorney, Agent, or Firm*—Birch, Stewart, Kolasch & Birch, LLP

(57) ABSTRACT

The present invention relates to a phenylalanine derivative of Formula (I) wherein $X^1$ is a halogen atom, $X^2$ is a halogen atom, Q is a $CH_2R$— is a carboxyl group which may be esterified; or a pharmaceutically acceptable salt thereof.

8 Claims, No Drawings

INHIBITORS OF ALPHA4 MEDIATED CELL ADHESION

This application is a Divisional of application Ser. No. 10/333,985 filed on Feb. 26, 2003, now U.S. Pat. No. 7,026,501 and for which priority is claimed under 35 U.S.C. § 120. application Ser. No. 10/333,985 is the national phase of PCT International Application No. PCT/US01/26594 filed on Aug. 27, 2001 under 35 U.S.C. § 371. This application also claims priority of application Ser. No. 60/229,128 filed in United States of America on Aug. 31, 2000 under 35 U.S.C. § 119. The entire contents of each of the above-identified applications are hereby incorporated by reference.

BACKGROUND OF THE INVENTION

1. Field of the Invention

The present invention relates to novel phenylalanine derivatives that are inhibitors of $\alpha_4$ (including $\alpha_4\beta_7$ and $\alpha_4\beta_1$) mediated adhesion which could be useful in treating conditions such as asthma, diabetes, rheumatoid arthritis, inflammatory bowel disease and other diseases involving leukocyte infiltration to the gastrointestinal tract or other epithelial lined tissues; such as, skin, urinary tract, respiratory airway and joint synovium.

The inhibitors of the present invention could also be useful in treating conditions involving leukocyte infiltration to other tissues including lung, blood vessels, heart and nervous system as well as transplanted organs such as kidney, liver, pancreas, heart and intestine, and blood vessels.

2. Description of the Related Art

The adhesion of leukocyte to endothelial cells or extracellular matrix proteins is a fundamental process for immunity and inflammation and involves multiple adhesive interactions. The earliest events in this process include leukocyte rolling followed by changes in integrin avidity, which lead to subsequent firm adhesion (for reviews see Butcher, *Cell* 67:1033-1036 (1991); Harlan, *Blood* 3:513-525 (1985); Hemler, *Annu. Rev. Immunol.* 8:365-400 (1990); Osborn, *Cell* 62:3-6 (1990); Shimizu et al., *Immunol. Rev.* 114:109-143 (1990); Springer, *Nature* 346:425-434 (1990); and Springer, *Cell* 76:301-314 (1994)). In response to chemotactic factors, the leukocytes must migrate through two adjacent endothelial cells and into tissues that are composed, in part, of the extracellular matrix protein fibronectin (FN) (see Wayner et al., *J. Cell Biol.* 105:1873-1884 (1987)) and collagen (CN) (see Bornstein et al., *Ann. Rev. Biochem.* 49:957-1003 (1980); and Miller, Chemistry of the collagens and their distribution, in "Extracellular Matrix Biochemistry", K. A. Piez and A. H. Reddi, editors, Elsevier, Amsterdam, 41-78 (1983)). Important recognition molecules that participate in these reactions belong to the integrin gene superfamily (for reviews see Hemler, *Annu. Rev. Immunol.* 8:365-400 (1990); Hynes, *Cell* 48:549-554 (1987); Shimizu et al., *Immunol. Rev.* 114:109-143 (1990); and Springer, *Nature* 346:425-434 (1990)).

Integrins are heterodimers composed of non-covalently associated subunits, referred to as the alpha ($\alpha$) and beta ($\beta$) subunits (for reviews see Hemler, *Annu. Rev. Immunol.* 8:365-400 (1990); Hynes, *Cell* 48:549-554 (1987); Shimizu et al., *Immunol. Rev.* 114:109-143 (1990); and Springer, *Nature* 346:425-434 (1990)). To date, 8 integrin $\beta$ subunits have been identified which can associate with 16 distinct a subunits to form 23 distinct integrins. The $\alpha_4\beta_1$ integrin, also known as VLA-4 (Very Late Antigen-4), is expressed on a variety of cells including lymphocytes, monocytes and eosinophils (see Hemler et al., *J. Bio. Chem.* 262:11478-11485 (1987); and Bochner et al., *J. Exp. Med.* 173:1553-1556 (1991)) and may have an important role in the recruitment of these cells during inflammation. VLA-4 is a receptor for vascular cell adhesion molecule-1 (VCAM-1) (Elices et al., *Cell* 60:577-584 (1990)) and the connecting segment 1 (CS-1), an alternatively spliced region of the FN A chain (Wayne et al., *J. Cell Biol.* 109:1321-1330 (1989)). The $\beta_7$ integrin subunit, first cloned by Erle et al. (Erle et al., *J. Biol. Chem.* 266:11009-11016 (1991)), is expressed only on leukocytes and is known to associate with two distinct a subunits, $\alpha_4$ (Ruegg et al., *J. Cell Biol.* 117:179-189 (1992)) and $\alpha E$ (Cerf-Bensussan et al., *Eur. J. Immunol.* 22:273-277 (1992); and Kilshaw et al., *Eur. J. Immunol.* 21:2591-2597 (1991)).

The $\alpha_4\beta_7$ complex has three known ligands (VCAM-1, CS-1, MAdCAM-1). One ligand which shows unique specificity for $\alpha_4\beta_7$ is Mucosal Addressin Cell Adhesion Molecule-1 (MAdCAM-1) (see Andrew et al., *J. Immunol.* 153: 3847-3861 (1994); Briskin et al., *Nature* 363:461-464 (1993); and Shyjan et al., *J. Immunol.* 156:2851-2857 (1996)). MAdCAM-1 is highly expressed on Peyer's patch high endothelial venules, in mesenteric lymph nodes, and on gut lamina propria and mammary gland venules (Berg et al., *Immunol. Rev.* 105:5-18 (1989)). Integrin $\alpha_4\beta_7$ and MAdCAM-1 have been shown to be important in regulating lymphocyte trafficking to normal intestine (Holzmann et. al., *Cell* 56:37-46 (1989)).

The second ligand for $\alpha_4\beta_7$ is CS-1 (see Guan et al., *Cell* 60:53-61 (1990); and Wayner et al., *J. Cell Biol.* 109:1321-1330 (1989)). The cell-binding site within CS-1 is composed of 25 amino acids where the carboxy terminal amino acid residues, BILDVPST, form the recognition motif (see Komoriya et al., *J. Biol. Chem.* 266:15075-15079 (1991); and Wayner et al., *J. Cell Biol.* 116:489-497 (1992)).

The third ligand for $(\alpha_4\beta_7$ is vascular cell adhesion molecule-1 (VCAM-1), a cytokine inducible protein expressed on endothelial cells (see Elices et al., *Cell* 60:577-584 (1990); and Ruegg et al., *J. Cell Biol.* 117:179-189 (1992)). It remains to be unequivocally shown whether MAdCAM-1, VCAM-1 and CS-1 bind to the same site on $\alpha_4\beta_7$. Using a panel of Monoclonal antibodies, Andrew et al. showed that $\alpha_4\beta_7$ interaction with its three ligands involves distinct but overlapping epitopes (Andrew et al., *J. Immunol.* 153:3847-3861 (1994)). VCAM-1 and CS-1 (see Elices et al., *Cell* 60:577-584 (1990)) are two ligands which are shared by $\alpha_4\beta_7$ and $\alpha_4\beta_1$. In addition, $\alpha_4\beta_1$ is also known to bind to osteopontin, a protein upregulated in arteriosclerotic plaques (see Bayless et al., *J. Cell Science* 111:1165-1174 (1998)).

Utility of the Invention

A number of in vivo studies indicate that the $\alpha_4$ integrins ($\alpha_4\beta_1/(\alpha_4\beta_7)$ play a critical role in the pathogenesis of a variety of diseases. Monoclonal antibodies directed against $\alpha_4$ have been tested in a variety of disease models. Efficacy of anti-$\alpha_4$ antibody was demonstrated in rat and mouse models of experimental autoimmune encephalomyelitis (see Baron et al., *J. Exp. Med.* 177:57-68 (1993); and Yednock et al., *Nature* 356:63-66 (1992)). A significant number of studies have been done to evaluate the role of $\alpha_4$ in allergic airways (see Abraham et al., *J. Clin. Invest.* 93:776-787 (1994); Bochner et al., *J. Exp. Med.* 173:1553-1556 (1991); Walsh et al., *J. Immunol.* 146:3419-3423 (1991); and Weg et al., *J. Exp. Med.* 177:561-566 (1993)). For example, monoclonal antibodies to $\alpha_4$ were effective in several lung antigen challenge models (see Abraham et al., *J. Clin. Invest.* 93:776-787 (1994); and Weg et al., *J. Exp. Med.* 177:561-566 (1993)). The cotton-top tamarin, which experiences spontaneous chronic colitis, showed a significant attenuation of colitis when anti-$\alpha_4$ antibody or anti-$\alpha_4\beta_7$ antibody was administered (see Bell et al., *J. Immunol.*

151:4790-4802 (1993); Podolsky et al., *J. Clin. Invest.* 92:372-380 (1993); and Hesterberg et al., *Gastroenterology* 111:1373-1380 (1996)). In scid mice reconstituted with $CD45RB^{high}$ $CD4^+$ T cells, monoclonal antibodies to $\beta_7$ or MAdCAM-1 blocked recruitment of lymphocytes to the colon and reduced the severity of inflammation in the colon as judged histologically (see Picarella et al., *J. Immunol.* 158: 2099-2106 (1997)). Monoclonal antibodies to $\alpha_4$ inhibit insulitis and delay the onset of diabetes in the non-obese diabetic (NOD) mouse (see Baron et al., *J. Clin. Invest.* 93:1700-1708 (1994); Burkly et al., *Diabetes* 43:529-534 (1994); and Yang et al., *Proc. Natl. Acad. Sci. USA* 90:10494-10498 (1993)). Other diseases where $\alpha_4$ has been implicated include rheumatoid arthritis (see Laffon et al., *J. Clin. Invest.* 88:546-552 (1991); and Morales-Ducret et al., *J. Immunol.* 149:1424-1431 (1992)), atherosclerosis (see Cybulsky et al., *Science* 251:788-791 (1991)), allograft rejection (Isobe et al., *J. Immunol.* 153:5810-5818 (1994)), and nephritis (Allen et al., *J. Immunol.* 162:5519-5527 (1999)). Delayed type hypersensitivity reaction (see Issekutz, *J. Immunol.* 147:4178-4184 (1991)), contact hypersensitivity response (see Chisholm et al., *Eur. J. Immunol.* 23:682-688 (1993); and Ferguson et al., *J. Immunol.* 150:1172-1182 (1993)) and intimal hyperplasia (Lumsden et al., *J. Vasc. Surg.* 26:87-93 (1997)) are also blocked by anti-$\alpha_4$ antibodies. For an excellent review of in vivo studies implicating $\alpha_4$ in disease, see Lobb et al., *J. Clin. Invest.* 94:1722-1728 (1995).

Leukocyte adhesion to inflamed synovium was suggested to be dominated by $\alpha_4\beta_1$/VCAM-1 interactions, however, increased numbers of $\alpha_4\beta_7$ positive T cells were also found in the synovial membrane of rheumatoid arthritis patients (McMurray, *Semin. Arthritis Rheum.* 25:215-233 (1996)) and it was suggested that the augmented expression of $\alpha_4\beta_7$ may contribute to the development and perpetuation of this disease (see Lazarovits et al., *J. Immunol.* 151:6482-6489 (1993)). In the NOD mouse, MAdCAM-1 was expressed on high endothelial venules in inflamed islets within the pancreas suggesting a role for $\alpha_4\beta_7$ in diabetes (see Yang et al., *Diabetes* 46:1542-1547 (1997)). The expression of $\alpha_4\beta_1/\beta_4\beta_7$ on a variety of leukocytes and the presence of $\alpha_4\beta_1/\alpha_4\beta_7$ positive cells in diseased tissues imply that the two receptors may play important roles in cellular recruitment to a number of sites of inflammation. For example, monoclonal antibodies to $\alpha_4$ were effective in several lung antigen challenge models such as ovalbumin-induced asthma in mice, rats and guinea-pigs (See Pretolani et al., *J. Eyp. Med.* 180: 795-805 (1994), Fryer et al., *J. Clin. Invest.* 99:2036-2044 (1997); and Henderson et al., *J. Clin. Invest.* 100: 3083-3092 (1997)). The expression of $\alpha_4\beta_7$ and $\alpha_4\beta_1$ on lymphocytes and eosinophils, together with in vitro studies showing that ($\alpha_4\beta_7/\alpha_4\beta_1$) mediates human eosinophil adhesion to VCAM-1, CS-1 and MAdCAM-1 (Walsh et al., *Immunology* 9:112-119 (1996)), suggests that $\alpha_4$ is a suitable therapeutic target for the treatment of asthma. Collectively, these data suggest that integrins $\alpha_4\beta_7$ and $\alpha_4\beta_1$ may play an important role in a variety of inflammatory diseases.

The use of monoclonal antibodies against integrins in vivo has demonstrated that a number of integrins are indeed valid therapeutic targets for inflammatory, immune-mediated diseases, cardiovascular diseases and in organ transplantation.

Also, it has been described that an orally bioavailable, non-peptide small molecule antagonist of $\alpha_4$ could be useful in treating or preventing conditions such as asthma, inflammatory bowel disease, rheumatoid arthritis, multiple sclerosis and other diseases (see WO99/36393).

The objective here was to define an orally bioavailable and potent small molecule antagonist of $\alpha_4$ integrins. Small molecules that are potent inhibitors of $\alpha_4$ mediated adhesion to either MAdCAM-1, VCAM-1, or CS-1 and which could be useful for the treatment or prevention of inflammatory diseases and/or allergic diseases are disclosed.

SUMMARY OF THE INVENTION

The present invention relates to a novel phenylalanine derivative of Formula [I]:

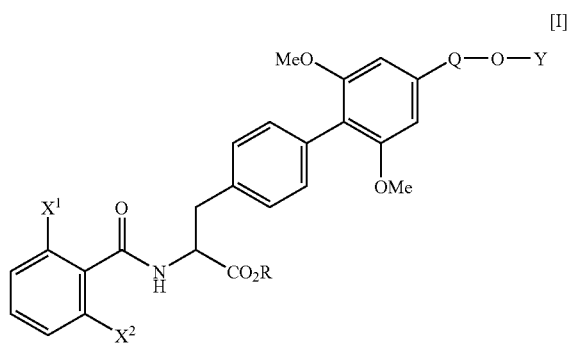

wherein $X^1$ is a halogen atom, $X^2$ is a halogen atom, Q is a —$CH_2$— group or a —$(CH_2)_2$— group, Y is a $C_{1-6}$ alkyl group, and $CO_2R$ is a carboxyl group which may be esterified; or a pharmaceutically acceptable salt thereof.

The present invention also relates to a pharmaceutical composition comprising therapeutically effective amount of a compound of Formula [I] or a pharmaceutically acceptable salt thereof.

Further, the present invention also relates to a method for treating or preventing conditions caused by $\alpha_4$ integrins (including $\alpha_4\beta_7$ and $\alpha_4\beta_1$) mediated cell adhesion which comprises administering a compound of Formula [I] or a pharmaceutically acceptable salt thereof.

DETAILED DESCRIPTION OF THE INVENTION

The compound of the present invention may exist in the form of optical isomers based on the asymmetric atom thereof, and the present invention includes these optical isomers and mixtures thereof.

In an embodiment of the present invention, a carboxyl group which may be esterified includes a carboxyl group and an esterified carboxyl group which may be hydrolyzed in a body to afford a carboxyl group. Examples of such esterified carboxyl group are a substituted or unsubstituted $C_{2-7}$ alkoxycarbonyl group such as methoxycarbonyl group, benzyloxycabonyl group, p-aminobenzyloxycarbonyl group and the like.

In an embodiment of the present invention, the R/S configuration of a bond need not be fixed. The compound of the present invention may be a compound with a sole configuration or a mixture with different configurations.

Among the compounds of the present invention, preferable compounds are compounds of Formula [I-1]:

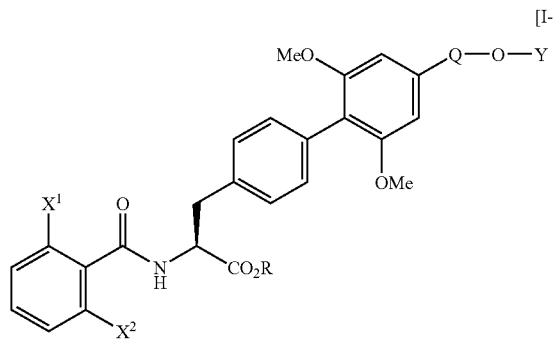

wherein symbols are the same as defined above.

In a more preferred embodiment of the compound [I-1], $X^1$ is chlorine atom or fluorine atom, $X^2$ is chlorine atom or fluorine atom, Y is a $C_{1-4}$ alkyl group, and $CO_2R$ is a carboxyl group or a $C_{2-7}$ alkoxycarbonyl group.

In a further preferred embodiment of the compound [I-1], $X^1$ is chlorine atom or fluorine atom, $X^2$ is chlorine atom or fluorine atom, Q is a —$CH_2$— group, Y is methyl group, ethyl group, or n-propyl group, and $CO_2R$ is a carboxyl group, methoxycarbonyl group, ethoxycarbonyl group, or tert-butoxycarbonyl group.

Especially preferable compounds are compounds of Formula [I-1] wherein $X^1$ is fluorine atom, $X^2$ is chlorine or fluorine atom, Q is a —$CH_2$— group, Y is methyl or ethyl group, and $CO_2R$ is a carboxyl group or a $C_{2-7}$ alkoxycarbonyl group such as methoxycarbonyl group and ethoxycarbonyl group.

Most preferable compounds of the present invention may be selected from:
N-(2,6-Difluorobenzoyl)-4-(2,6-dimethoxy-4-ethoxymethylphenyl)-L-phenylalanine [i.e., (2S)-2-[(2,6-difluorobenzoyl)amino]-3-[4-(2,6-dimethoxy-4-ethoxymethylphenyl)phenyl]propanoic acid];
N-(2-Chloro-6-fluorobenzoyl)-4-(2,6-dimethoxy-4-ethoxymethylphenyl)-L-phenylalanine [i.e., (2S)-2-[(2-chloro-6-fluorobenzoyl)amino)-3-[4-(2,6-dimethoxy-4-ethoxymethylphenyl)phenyl]propanoic acid];
N-(2-Chloro-6-fluorobenzoyl)-4-(2,6-dimethoxy-4-methoxymethylphenyl)-L-phenylalanine [i.e., (2S)-2-[(2-chloro-6-fluorobenzoyl)amino]-3-[4-(2,6-dimethoxy-4-methoxymethylphenyl)phenyl]propanoic acid];
N-(2,6-Difluorobenzoyl)-4-(2,6-dimethoxy-4-methoxymethylphenyl)-L-phenylalanine [i.e., (2S)-2-[(2,6-difluorobenzoyl)amino]-3-[4-(2,6-dimethoxy-4-methoxymethylphenyl)phenyl]propanoic acid];
or a $C_{1-6}$ alkyl ester thereof;
or a pharmaceutically acceptable salt thereof.

The compound of the present invention may be used either in a free form or in a form of pharmaceutically acceptable salts thereof. Pharmaceutically acceptable salts include a salt with an inorganic base, an organic base or a basic amino acid (e.g., an alkali metal salt such as a sodium salt and a potassium salt; an alkali earth metal salt such as magnesium salt and calcium salt; or a salt with an amine such as an ammonium salt, triethylammonium salt, a salt with lysine and the like) and a salt with an inorganic acid or an organic acid (e.g., hydrochloride, sulfate, nitrate, hydrobromide, methanesulfonate, p-toluenesulfonate, acetate, maleate). Pharmaceutically acceptable salts also include an intramolecular salt thereof, or a solvate or hydrate thereof, as well.

The characteristics of the present compound are the introduction of a $C_{1-6}$ alkoxy substituted $C_{1-2}$ alkyl group at the 4'-position of the biphenyl nucleus and the combination of the dihalo-substituted benzoyl group and 2',6'-di($C_{1-6}$ alkoxy)-4'-($C_{1-6}$ alkoxy substituted $C_{1-2}$ alkyl)biphenyl nucleus, where such characteristics are not specifically described in prior publications.

The compound of the present invention has potent inhibitory activity against $\alpha_4$ mediated cell adhesion, and shows excellent bioavailability after oral administration which reflects the overall improvement in: a) metabolic stability, b) plasma protein binding and c) aqueous solubility. In particular, the introduction of a $C_{1-6}$ alkoxy substituted $C_{1-2}$ alkyl group at the 4'-position of the biphenyl nucleus reduces the fast metabolism that was observed with some of the compounds described in prior publications. The compound of the present invention reduces hepatic clearance thereby improving the bioavailability.

The compound of the present invention, therefore, shows excellent in vivo improvements against the unfavorable conditions caused by the $\alpha_4$ mediated cell adhesion.

The compound of the present invention can be used for a method of treating or preventing $\alpha_4$ (including $\alpha_4\beta_1$ and $\alpha_4\beta_7$) adhesion mediated conditions in a mammal such as a human.

In another aspect, the compound of the present invention can be used for a method of treating an individual (e.g., a mammal, such as a human or other primate) suffering from a disease associated with leukocyte (e.g., lymphocyte, monocyte) infiltration to tissues (including recruitment and/or accumulation of leukocytes in tissues) which express the molecule MAdCAM-1 and/or VCAM-1. For example, inflammatory diseases, including diseases which are associated with leukocyte infiltration to the gastrointestinal tract (including gut-associated endothelium), other mucosal tissues, or tissues expressing the molecule MAdCAM-1 (e.g., gut-associated tissues, such as venules of the lamina propria of the small and large intestine; and mammary gland (e.g., lactating mammary gland)), can be treated according to the present method. Similarly, an individual suffering from a disease associated with leukocyte infiltration to tissues as a result of binding of leukocytes to cells (e.g., endothelial cells) expressing the molecule VCAM-1 can be treated according to the present invention.

The method for treating or preventing $\alpha_4$-dependent (including $\alpha_4\beta_1$ and $\alpha_4\beta_7$) adhesion mediated conditions or diseases associated with leukocyte infiltration may comprise administering to a mammal or a human patient an effective amount of the compound of the present invention in admixture with a pharmaceutically acceptable carrier or diluent.

The compound of the present invention, accordingly, can be used to treat or prevent such inflammatory conditions as rheumatoid arthritis (RA); asthma; allergic conditions such as rhinitis; adult respiratory distress syndrome; AIDS-dementia; Alzheimer's disease; cardiovascular diseases; thrombosis or harmful platelet aggregation; reocclusion following thrombolysis; reperfusion injury; psoriasis; skin inflammatory diseases such as eczema, contact dermatitis and atopic dermatitis; diabetes (e.g., insulin-dependent diabetes mellitus, autoimmune diabetes); multiple sclerosis; systemic lupus erythematosus (SLE); inflammatory bowel disease such as ulcerative colitis, Crohn's disease (regional enteritis) and pouchitis (for example, resulting after proctocolectomy and ileoanal anastomosis); diseases associated with leukocyte infiltration to the gastrointestinal tract such as Celiac disease, nontropical Sprue, enteropathy associated with seronegative arthropathies, lymphocytic or collagenous colitis, and eosinophilic gastroenteritis; diseases associated with leukocyte infiltration to other epithelial lined tissues, such as skin, urinary tract, respiratory airway, and joint synovium; pancreatitis; mastitis (mammary gland); hepatitis; cholecystitis; cholangitis or pericholangitis (bile duct and surrounding tissue of the liver); bronchitis; sinusitis; inflammatory diseases of the lung which result in interstitial fibrosis, such as hypersensitivity pneumonitis; collagen disease (in SLE and RA); sarcoidosis; osteoporosis; osteoarthritis; atherosclerosis; neoplastic diseases including metastasis of neoplastic or cancerous growth; wound (wound healing enhancement); certain eye diseases such as retinal detachment, allergic conjunctivitis and autoimmune uveitis; Sjogren's syndrome; rejection (chronic and acute) after transplantation; host vs. graft or graft vs. host diseases; intimal hyperplasia; arteriosclerosis (including graft arteriosclerosis after transplantation); reinLarction or restenosis after surgery such as percutaneous transluminal coronary angioplasty (PTCA) and percutaneous transluminal artery recanalization; nepliritis; tumor angiogenesis; malignant tumor; multiple myeloma and myeloma-induced bone resorption; and central nervous system injury such as stroke, traumatic brain injury and spinal cord injury.

The method can be preferably used for the treatment or prevention of asthma, allergic conditions such as rhinitis, inflammatory bowel disease such as ulcerative colitis and Crohn's disease, rheumatoid arthritis, atopic dermatitis, multiple sclerosis and rejection after transplantation.

Compounds suitable for use in therapy can be evaluated in vivo, using suitable animal models. Suitable animal models of inflammation have been described in publications. For example, NOD mice provide an animal model of insulin-dependent diabetes mellitus. CD45RB$^{Hi}$ SCID mice model provide a model with similarity to both Crohn's disease and ulcerative colitis (Powrie et al., *Immunity* 1:553-562 (1994)). Cotton-top tamarins develop spontaneous, often chronic, colitis that clinically and histologically resembles ulcerative colitis in humans (Madara et al., *Gastroenterology* 88:13-19 (1985)). The dextran sodium sulfate (DSS) model of murine colitis is introduced by adding DSS in the drinking water. The physiological and histological changes of the DSS colon have been well described in the literature and are reminiscent of human ulcerative colitis (Cooper et al., *Laboratory Investig.* 69:238-249 (1993)). IL-10 knockout mice that develop intestinal lesions similar to those of human inflammatory bowel disease have also been described (Strober et al., *Cell* 75:203-205 (1993)).

While it is possible for the compound of the present invention to be administered alone, it is preferable to present it as a pharmaceutical composition comprising a therapeutically effective amount of the compound of Formula [I] and a pharmaceutically acceptable carrier or diluent.

The carrier must be acceptable in the sense of being not deleterious to the recipient thereof. The pharmaceutically acceptable carrier or diluent may be, for example, binders (e.g., syrup, gum arabic, gelatin, sorbitol, tragacanth, polyvinylpyrrolidone), excipients (e.g., lactose, sucrose, corn starch, potassium phosphate, sorbitol, glycine), lubricants (e.g., magnesium stearate, talc, polyethylene glycol, silica) disintegrators (e.g., potato starch), wetting agents (e.g., sodium laurylsulfate), and the like.

The pharmaceutical compositions include those in a form suitable for oral, pulmonary, ophthalmic, rectal, parenteral (including subcutaneous, intramuscular, and intravenous), intra-articular, topical, nasal inhalation (e.g., with an aerosol) or buccal administration. These formulations are understood to include long-acting formulations known in the art of pharmacy. Oral and parenteral administrations are preferred modes of administration.

The pharmaceutical composition may conveniently be presented in unit dosage form and may be prepared by any of the methods well known in the art of pharmacy. In general, the formulations are prepared by uniformly and intimately bringing the active ingredient into association with a liquid carrier or a finely divided solid carrier or both, and then, if necessary, shaping the product into the desired form.

Compositions of the present invention suitable for oral administration may be in the form of discrete units such as capsules, cachets, tablets, or lozenges, each containing a predetermined amount of the compound of the present invention, in the form of a powder or granules, or in the form of a solution or suspension in an aqueous liquid. Formulations for other uses could involve a nonaqueous liquid; in the form of an oil-in-water emulsion or a water-in-oil emulsion; in the form of an aerosol; or in the form of a cream or ointment or impregnated into a transdermal patch for use in administering the compound of the present invention transdermally, to a patient in need thereof. The compound of the present invention may also be administered to a patient in need thereof in the form of a bolus, electuary, or paste.

The compound of the present invention can be administered to a patient in need thereof in amounts sufficient to reduce or prevent $\alpha_4$-mediated cell adhesion. In another aspect, the compound of the present invention can be administered to the patient in amounts sufficient to achieve the desired therapeutic and/or prophylactic effect, or amounts sufficient to reduce or prevent MAdCAM-1/VCAM-1 mediated binding to a MAdCAM-1/VCAM-1 ligand, thereby inhibiting leukocyte adhesion and infiltration and associated cellular responses.

The compounds and compositions of the present invention can be administered to patients suffering from a condition listed herein before in an amount which is effective to fully or partially alleviate undesired symptoms of the condition. The symptoms may be caused by leukocyte adhesion or cell activation, which would typically be expected to occur as a result of increased VCAM-1 and/or MAdCAM-1 expression on the surface of endothelial cells. Increased VCAM-1, MAdCAM-1 and/or CS-1 expression can be due to a normal inflammation response or due to abnormal inflammatory states. In either case, an effective dose of a compound of the invention may reduce the increased cell adhesion due to increased VCAM-1 and/or MAdCAM-1 expression by endothelial cells. Reducing the adhesion observed in the disease state by 50% can be considered an effective reduction in adhesion. More preferably, a reduction in ex vivo adhesion by 90%, is achieved. Most preferably, adhesion mediated by VCAM-1, MAdCAM-1 and/or CS-1 interaction is abolished by an effective dose. Clinically, in some instances, effects of the compound can be observed as a decrease in leukocyte infiltration into tissues or sites of injury or inflammation. To achieve a therapeutic effectiveness, then, the compounds or compositions of the present invention are administered to provide a dose effective to reduce or eliminate leukocyte adhesion or cell activation to alleviate undesired symptoms.

The amount of the compound [I] required to achieve a therapeutic effect will vary with the particular compound, the route of administration, the age, sex, weight, and condition of the subject to be treated, and the particular disorder or disease to be treated. A suitable daily dose of the compound [I], or a pharmaceutically acceptable salt thereof, for a mammalian subject suffering from, or likely to suffer from, any condition as described herein is from 0.1 to 100 mg per kilogram body weight of the mammalian subject, preferably 0.3 to 30 mg/kg of mammal body weight. In the case of parenteral administration, the dose may be in the range of 0.1 to 10 mg of the compound per kilogram body weight, preferably 0.3 to 3 mg/kg of mammal body weight. In the case of oral dosing, a suitable (daily) dose may be in the range of 1 to 100 mg of the compound per kilogram body weight, but preferably 2 to 30 mg of the compound per kilogram, the most preferred dosage being 1 to 10 mg/kg of mammal body weight administered two to three times daily. In the case of topical administration, e.g., to the skin or eye, a suitable dose of a compound of Formula [I], or a pharmaceutically acceptable salt thereof, may be in the range of 0.1 to 100 μg of the compound per kilogram.

The compound of Formula [I] or a pharmaceutically acceptable salt thereof can be prepared by the steps comprising:

(1) converting a compound of Formula [II]:

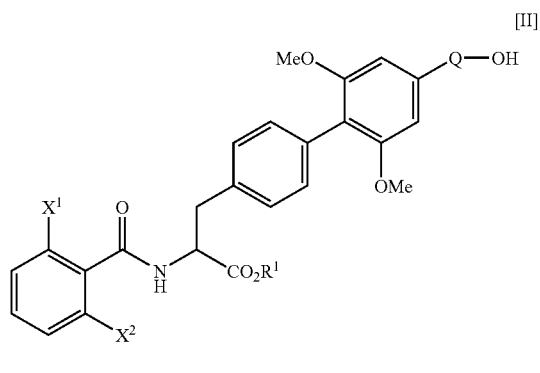

[II]

wherein $CO_2R^1$ is an esterified carboxyl group, and the other symbols are the same as defined above, into a compound of Formula [Ia]:

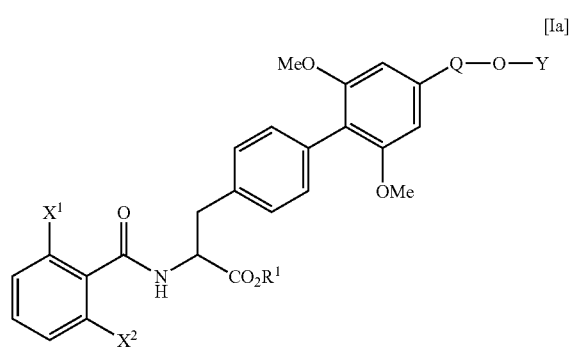

[Ia]

wherein the symbols are the same as defined above,
(2) converting the esterified carboxyl group of the compound [Ia] into a carboxyl group, if necessary, and
(3) converting the resulting compound into a pharmaceutically acceptable salt thereof, if further desired.

Step 1: The conversion of the compound [II] into the compound [Ia] can be carried out by one of the Methods A to D described hereinafter.

Step 2: The conversion of the esterified carboxyl group $CO_2R^1$ into a carboxyl group can be carried out by a conventional method, which is selected according to the type of the esterified carboxyl group to be converted, for example, hydrolysis using a base (e.g., an alkali metal hydroxide such as LiOH and NaOH) or an acid (e.g., HCl), treatment with an acid (e.g., TFA), and the like.

Step 3: The conversion of the resulting compound [I] into a pharmaceutically acceptable salt thereof can be carried out by a conventional method using a base (e.g., inorganic base such as NaOH, organic base such as triethylamine or basic amino acid such as lysine) or an acid (e.g., inorganic acid such as HCl, $HNO_3$ and $H_2SO_4$, organic acid such as acetic acid and maleic acid, or acidic amino acid such as aspartic acid and glutamic acid).

The conversion of the compound [II] to the compound [Ia] can be achieved by one of the following methods (Methods A-D):

Method A:

The compound [Ia], wherein Q is a —$CH_2$— group, can be prepared by:
(1) oxidizing the compound [II] to afford a compound of Formula [III]

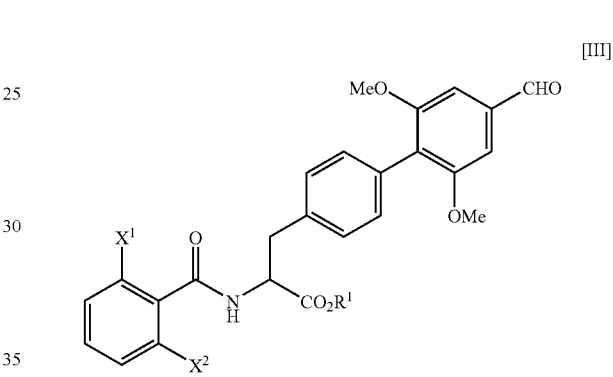

[III]

wherein the symbols are the same as defined above, and
(2) reductively condensing the compound [III] with a compound of Formula [IV]:

Y—OH  [IV]

wherein Y is the same as defined above.

Step 1: The oxidation reaction can be carried out by a conventional method using an oxidizing agent with or without a base in a suitable solvent.

The oxidizing agent can be selected from conventional oxidizing reagents such as $MnO_2$, $SO_3$.pyridine, $KMnO_4$, PCC, PDC and the like.

The base can be selected from conventional organic bases such as trialkylamine (e.g., $Et_3N$, DIEA).

The solvent can be selected from any one which does not disturb the oxidation reaction, for example, halogenomethanes (e.g., $CH_2Cl_2$, $CHCl_3$), aromatic hydrocarbons (e.g., benzene, toluene), DMSO, $H_2O$ or a mixture thereof.

The reaction can be carried out at a temperature of −50° C. to 50° C., preferably at room temperature.

Step 2: The condensation of the compound [III] with the compound [IV] can be carried out in the presence of a reducing agent and a dehydrating reagent in a solvent or without a solvent.

The reducing agent can be selected from conventional reducing agents such as trialkylsilane (e.g., triethyl-silane) and the like.

The dehydrating reagent includes sulfuric acid, trifluoroacetic acid and the like.

The solvent can be selected from any one which does not disturb the reaction, for example, ethers (e.g., dioxane, THF), aromatic hydrocarbons (e.g., benzene toluene), halogenomethanes (e.g., $CH_2Cl_2$ and $CHCl_3$) or a mixture thereof.

The reaction can be carried out at a temperature of $-50°$ C. to $50°$ C., preferably at $0°$ C. to room temperature.

Method B:

The compound [Ia] can be prepared by:

(1) converting the compound [II] into a compound of Formula [V]:

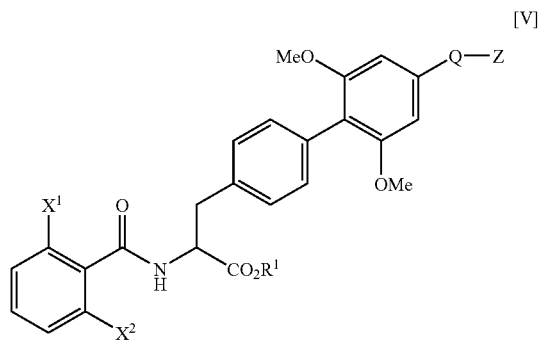

wherein Z is a leaving group and the other symbols are the same as defined above, and (2) reacting the compound [V] with the compound [IV].

As the leaving group of Z, a halogen atom (e.g., chlorine atom, bromine atom and iodine atom), an alkanesulfonyloxy group (e.g., methanesulfonyl group) or an arylsulfonyloxy group (e.g., benzenesulfonyl group and p-toluenesulfonyl group) can be preferably used.

Step 1: The conversion of the compound [II] into the compound [V] can be carried out by halogenating or sulfonylating ne compound [II].

The halogenation reaction can be carried out by the conventional method using a halogenating reagent with or without a base in a suitable solvent.

The halogenating reagent can be selected from the conventional halogenating reagents such as phosphorus trihalide (e.g., phosphorous tribromide, phosphorous trichloride), and a combination of tetrahalomethane (e.g., $CBr_4$) and triphenylphosphine.

The base can be selected from conventional inorganic bases such as alkali metal carbonate (e.g., $Na_2CO_3$, $K_2CO_3$), alkali metal hydrogen carbonate (e.g., $NaHCO_3$, $KHCO_3$) and the like.

The solvent can be selected from any one which does not disturb the condensation reaction, for example, halogenomethanes (e.g., $CH_2Cl_2$, $CHCl_3$), ethers (e.g., dioxane, diethyl ether, THF), DMF, DMSO, or a mixture thereof.

The reaction can be carried out at a temperature of $-50°$ C. to $50°$ C., preferably at $0°$ C. to room temperature.

The sulfonylation reaction can be carried out by the conventional method using a sulfonylating reagent with a base in a suitable solvent.

The sulfonylating reagent can be selected from an alkanesulfonyl halide and an arylsulfonyl halide such as methanesulfonyl chloride, benzenesulfonyl chloride, p-toluenesulfonyl chloride and the like.

The base can be selected from an organic base (e.g., trialkylamine such as $Et_3N$, DIVA, DBU and 4-methyl morpholine, and pyridine), an alkali metal carbonate (e.g., $Na_2CO_3$, $K_2CO_3$), an alkali metal hydrogen carbonate (e.g., $NaHCO_3$, $KHCO_3$), an alkali metal hydroxide (e.g., NaOH, KOH), an alkaline earth metal hydroxide (e.g., $Ba(OH)_2$), and the like.

The solvent can be selected from any one which does not disturb the reaction, for example, halogenomethanes (e.g., $CH_2Cl_2$, $CHCl_3$), ethers (e.g., dioxane, diethyl ether, THF), DMF, DMSO, or a mixture thereof.

The reaction can be carried out at a temperature of $-50°$ C. to $50°$ C., preferably at $-20°$ C. to $0°$ C.

Step 2: The reaction of the compound [V] with the compound [IV] can be carried out in the presence or absence of a base and/or a dehalogenation reagent such as a silver compound (e.g., silver (I) oxide ($Ag_2O$) and silver oxide (AgO)) (see Ortiz et al., *Synth. Commun.* 23:749-756(1993)) in a suitable solvent or without a solvent.

Preferably, the reaction can be carried out in the presence of a silver compound without a base in a suitable solvent.

The base can be selected from conventional inorganic bases and organic bases such as alkali metal carbonate (e.g., $Na_2CO_3$, $K_2CO_3$), alkali metal hydrogen carbonate (e.g., $NaHCO_3$, $KHCO_3$), trialkylamine (e.g., $Et_3N$), pyridine and the like.

The solvent can be selected from any one which does not disturb the condensation reaction, for example, aromatic hydrocarbons (e.g., benzene, toluene), halogenomethanes (e.g., $CH_2Cl_2$, $CHCl_3$), ethers (e.g., dioxane, diethyl ether, THF), DMF, DMSO, MeCN, or a mixture thereof.

The reaction can be carried out at a temperature of room temperature to $100°$ C.

Method C:

The compound [Ia] can be prepared by alkylating the compound [II] with a compound of Formula [VI]:

wherein the symbols are the same as defined above.

The alkylation can be carried out in the presence or absence or a base and/or a dehalogenation reagent such as silver compound (e.g., silver (I) oxide ($Ag_2O$) and silver oxide (AgO)) (see Choi et al., *J. Med. Chem.* 39:1907-1916 (1996)) in a suitable solvent or without solvent. The reaction can be carried out in a similar manner as described in the Step 2 of Method B.

Method D:

The compound [Ia] can be prepared by condensing the compound [II] with the compound [IV]

The condensation reaction can be carried out in the presence of a dehydrating reagent in a suitable solvent or without solvent. The dehydrating reagent can be selected from conventional dehydrating reagents such as sulfuric acid, p-toluenesulfonic acid and the like.

The solvent can be selected from any one which does not disturb the condensation reaction, for example, aromatic hydrocarbons (e.g., benzene, toluene), halogenomethanes (e.g., $CH_2Cl_2$, $CHCl_3$), ethers (e.g., dioxane, diethyl ether, THF), DMF, DMSO, MeCN, or a mixture thereof.

The reaction can be carried out at a temperature of room temperature to $100°$ C.

The starting compound [II] can be prepared by one of the following methods (Methods E-G).

Method E:

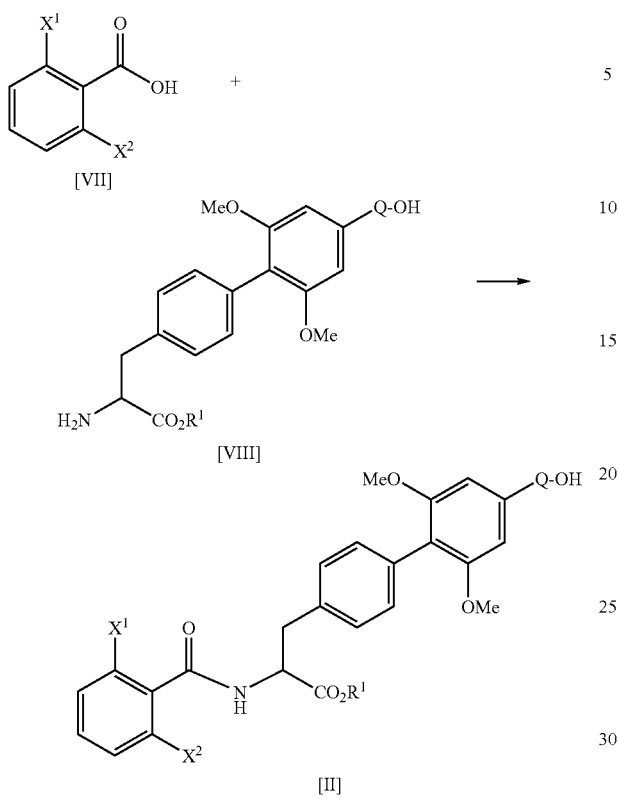

(In the above scheme, the symbols are the same as defined above.)

The compound [II] can be prepared by condensing a compound of Formula [VII], a salt thereof or a reactive derivative thereof, with a compound of Formula [VIII] or a salt thereof.

A salt of the compound [VII] and [VIII] includes, for example, a salt with an inorganic or organic acid (e.g., trifluoroacetate, hydrochloride, sulfate), a salt with an inorganic base (e.g., an alkali metal salt such as a sodium salt or a potassium salt, an alkaline earth metal salt such as a barium salt or calcium salt).

The condensation reaction can be carried out by a conventional method applied for a usual peptide synthesis.

The condensation reaction of the compound [VII] or a salt thereof with the compound [VIII] or a salt thereof can be carried out in the presence of a condensing reagent, with or without a base in a suitable solvent.

The condensing reagent can be selected from any one which can be used for a conventional peptide synthesis, for example, BOP—Cl, BOP reagent, DCC, EDC or CDI. The condensing reagent can be used with an activator (e.g., HOBt).

The base can be selected from an organic base (e.g., DIEA, DMAP, DBU, Et$_3$N, 4-Methyl morpholine), an alkali metal carbonate (e.g., Na$_2$CO$_3$, K$_2$CO$_3$), an alkali metal hydrogen carbonate (e.g., NaHCO$_3$, KHCO$_3$) an alkali metal hydroxide (e.g., NaOH, KOH) and the like.

The solvent can be selected from any one which does not disturb the condensation reaction, for example, AcOEt, CHCl$_3$, CH$_2$Cl$_2$, THF, DMF, H$_2$O or a mixture thereof. The reaction can be carried out at a temperature of −50° C. to 50° C., preferably at 0° C. to room temperature.

The condensation reaction of the compound [VIII] or a salt thereof with the reactive derivative of the compound [VII] is carried out in the presence or absence of a base in a solvent.

Examples of the reactive derivative of the compound [VII] are an acid halide (e.g., an acid chloride), a reactive ester (e.g., an ester with p-nitrophenol), an anhydride thereof, a mixed anhydride with other carboxylic acid (e.g., a mixed anhydride with acetic acid), and the like.

The base can be selected from an organic base (e.g., DIEA, DMAP, DBU, Et$_3$N), an alkali metal carbonate (e.g., Na$_2$CO$_3$, K$_2$CO$_3$), an alkali metal hydroxide (e.g., NaOH, KOH) and the like.

The solvent can be selected from any one which does not disturb the condensation reaction, for example, AcOEt, H$_2$O, CHCl$_3$, CH$_2$Cl$_2$, C$_2$H$_4$Cl$_2$, Et$_2$O, THF, DMF, CH$_3$CN, DMSO, benzene, toluene or a mixture thereof. The reaction can be carried out at a temperature of −30° C. to room temperature.

Method F:

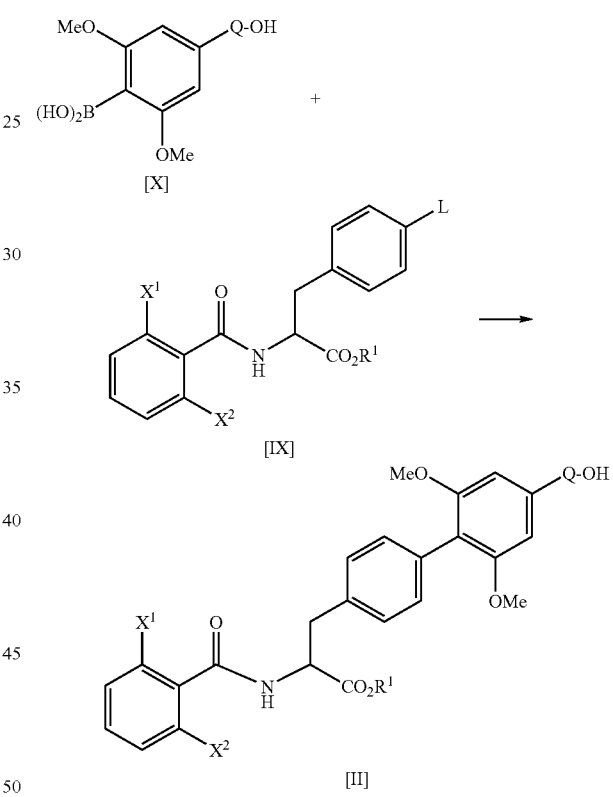

(In the above scheme, L is a leaving group and the other symbols are the same as defined above.)

The compound [II] can be prepared by reacting a compound of Formula [IX] with a compound of Formula [X].

Examples of the leaving group L may be a halogen atom and a trifluoromethanesulfonyloxy group.

The coupling reaction can be carried out by a conventional aryl coupling method, e.g., Suzuki coupling method (for reference see: Suzuki et al., *Synth. Commun.* 11:513 (1981); Suzuki, *Pure and Appl. Chem.* 57:1749-1758 (1985); Suzuki et al., *Chem. Rev.* 95:2457-2483 (1995); Shieh et al., *J. Org. Chem.* 57:379-381 (1992); and Martin et al., *Acta Chemica Scandinavica* 47:221-230 (1993)).

The coupling reaction can be carried out, for example, at a temperature of room temperature to 150° C., preferably at a temperature of 80° C. to 150° C., in the presence of a palladium catalyst (e.g., tetrakis(triphenylphosphine)-palladium, palladium(II) acetate, palladium(II) chloride), a phosphine ligand (e.g., triphenylphosphine, triethyl phosphite, trimethyl phosphite, triisopropyl phosphite) and a base (e.g., $K_2CO_3$, $Et_3N$, DIEA, Dabco, diisopropylamine, morpholine) in a suitable solvent. The solvent can be selected from any one which does not disturb the coupling reaction, for example, toluene, THF, DME, DMF, DMA, NMP, $H_2O$ or a mixture thereof.

Method G:

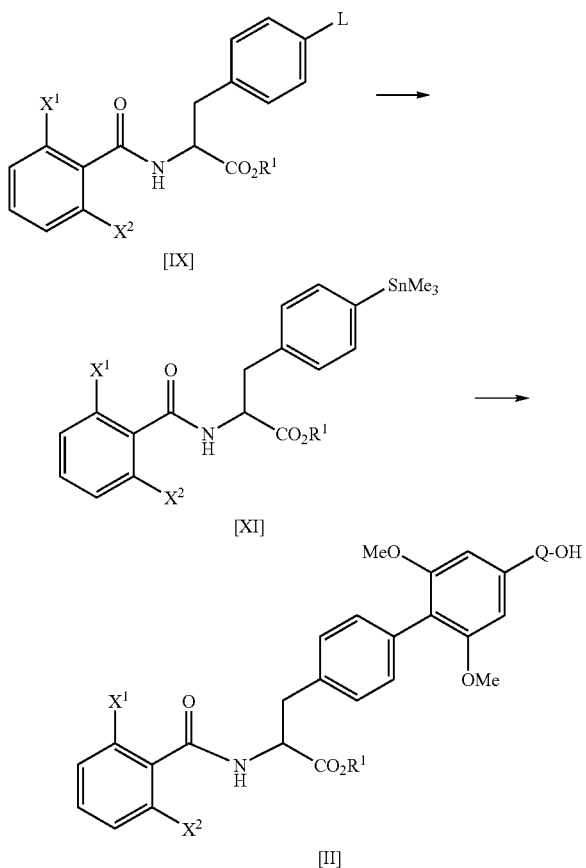

(In the above scheme, the symbols are the same as defined above.)

A compound of Formula [II] can be also prepared by:
(1) converting a compound [IX] to the corresponding organotin compound (e.g., the compound of Formula [XI]), and
(2) reacting the resulting compound with a compound of Formula [XII]:

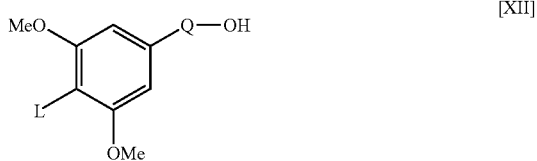

wherein the symbols are the same as defined above.

Step 1: The conversion of the compound [IX] to the corresponding organotin compound can be carried out, for example, by reacting the compound [IX] with a hexaalkylditin (e.g., hexamethylditin) at a temperature of room temperature to 150° C., preferably at a temperature of 80° C. to 110° C., in the presence of tetrakis(triphenylphosphine)palladium and an additive (e.g., LiCl) in a suitable solvent. The solvent can be selected from any one which does not disturb the coupling reaction, for example, dioxane, toluene, DME, DMF, $H_2O$ or a mixture thereof.

Step 2: The coupling reaction can be carried out by a conventional aryl coupling method, e.g., Stille coupling method (for reference see: Stille et al., *Angew. Chem. Int. Ed. Engl.* 25:508-524 (1986)).

The coupling reaction can be carried out, for example, at a temperature of room temperature to 150° C., preferably at a temperature of 80° C. to 120° C., in the presence of tetrakis (triphenylphosphine)palladium in a suitable solvent. The solvent can be selected from any one which does not disturb the coupling reaction, for example, toluene, DME, DMF, $H_2O$ or a mixture thereof.

The compound [IX] can be prepared by: (1) condensing a compound of Formula [XIII]:

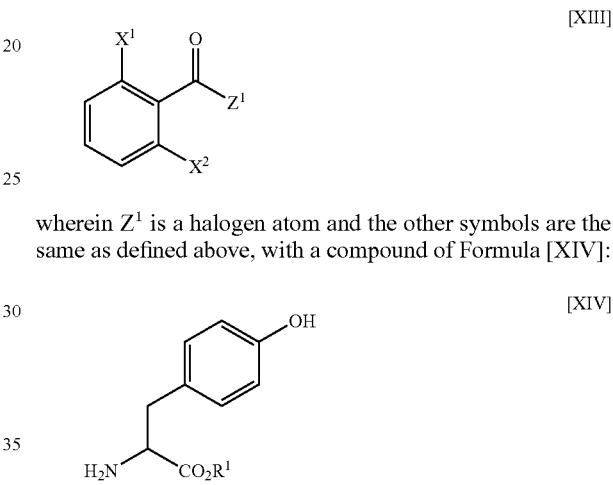

wherein $Z^1$ is a halogen atom and the other symbols are the same as defined above, with a compound of Formula [XIV]:

wherein $CO_2R^1$ is the same as defined above, or a salt thereof, by a conventional method similar to Method E; and (2) converting the hydroxyl group of the resulting compound into a leaving group by a conventional method. For example, the conversion of the hydroxyl group into trifluoromethanesulfonyloxy group can be carried out by using-triflic anhydride at −30° C. to 0° C. in the presence of a base (e.g., pyridine, $NEt_3$, DIEA) in a suitable solvent (e.g., $CH_2Cl_2$, $CHCl_3$, THF or a mixture thereof).

The compound [VIII] can be prepared by: (1) condensing a compound of Formula [XV]:

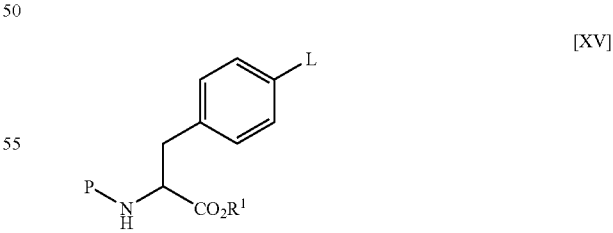

wherein P is a protecting group for an amino group and the other symbols are the same as defined above, with a compound [α] by a conventional aryl coupling method, and (2) removing the protecting group for the amino group of the resulting compound.

The protecting group for the amino group can be selected from conventional protecting groups for an amino group, for example, a substituted or unsubstituted aryl-$C_{2-7}$ alkoxycarbonyl group (e.g., benzyloxycarbonyl group, p-nitrobenzyloxycarbonyl group), a $C_{2-7}$ alkoxycarbonyl group (e.g., tert-butoxycarbonyl group) and the like.

The coupling reaction can be carried out in a similar manner as described for the reaction of the compound [IX] with the compound [α] in Method F.

The removal of the protecting group for the amino group can be carried out by a conventional method, which is selected according to the type of the protecting group to be removed, for example, catalytic reduction using a catalyst (e.g., palladium on activated carbon), treatment with an acid (e.g., TFA, HCl) and the like.

The compound [XV] wherein L is trifluoromethanesulfonyloxy group can be prepared by reacting the compound of Formula [XVI]:

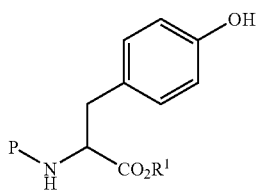

wherein the symbols are the same as defined above, with triflic anhydride in a similar manner as described in step (2) of the preparation of the compound [IX].

The compound [X] can be prepared by a conventional method (for reference, see: Kuivila et al., *J. Am. Chem. Soc.* 83:2159 (1961); Gerrard, The Chemistry of Boron, Academic Press, New York (1961); Muetterties, The Chemistry of Boron and its Compounds, Wiley, New York (1967); and Alamansa et al., *J. Am. Chem. Soc.* 116:11723-11736 (1994)). For example, the compound [X] can be prepared by:
(1) reacting a compound of Formula [XVII]:

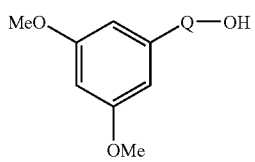

herein Q is the same as defined above, with an alkyl lithium (e.g., n-BuLi) at a temperature of −100° C. to room temperature in a suitable organic solvent (e.g., diethyl ether, THF or the mixture thereof), (2) reacting the resulting compound with trimethyl borate at a temperature of −100° C. to room temperature in a suitable organic solvent (e.g., diethyl ether, THF or the mixture thereof), and (3) hydrolyzing the resulting compound by a conventional method.

The hydrolysis can be carried out at 0° C. to room temperature in a suitable solvent (e.g., diethyl ether, THF, dioxane, $H_2O$ or the mixture thereof) in the presence of an acid (e.g., AcOH or citric acid) and water.

Throughout the present specification and claims, a halogen atom means chlorine atom, fluorine atom, bromine atom or iodine atom. And a $C_{1-6}$ alkyl group means a straight, branched or cycloalkyl group having 1 to 6 carbon atoms, preferably 1 to 4 carbon atoms, such as methyl, ethyl, n-propyl, n-butyl, isopropyl, cyclopropyl, tert-butyl and the like. A $C_{2-7}$ alkoxycarbonyl group means a straight, branched or cycloalkoxycarbonyl group having 2 to 7 carbon atoms, preferably 2 to 5 carbon atoms, such as methoxycarbonyl, ethoxycarbonyl, n-propoxycarbonyl, n-butoxycarbonyl, iso-propoxycarbonyl, cyclopropoxycarbonyl, tert-butoxycarbonyl and the like.

Abbreviations:
BOP—Cl: Bis(2-oxo-3-oxazolidinyl)phosphinic chloride
BOP reagent: Benzotriazol-1-yloxy-tris (dimethylamino)-phosphonium hexafluorophosphate
DCC: 1,3-Dicyclohexylcarbodiimide
EDC: 1-Ethyl-3-(3-dimethylaminopropyl)carbodiimide
THF: Tetrahydrofuran
DMF: N,N-Dimethylformamide
DMSO: Dimethyl sulfoxide
DMA: N,N-Dimethylacetamide
NMP: 1-Methyl-2-pyrrolidone
DIEA: Diisopropylethylamine
DMAP: 4-(N,N-Dimethylamino)pyridine
DBU: 1,8-Diazabicyclo(5.4.0]undec-7-ene
Dabco: 1,4-Diazabicyclo[2.2.2]octane
CDI: Carbonyldiimidazole
HOBT: 1-Hydroxybenzotriazole
TFA: Trifluoroacetic acid
DME: 1,2-Dimethoxyethane
PCC: Pyridinium chlorochromate
PDC: Pyridinium dichromate
Ac: Acetyl
Me: Methyl
Et: Ethyl
Pr: Propyl
Bu: Butyl
Ph: Phenyl
EtOAc: Ethyl acetate (=AcOEt)

EXAMPLES

Example 1

N-(2,6-Dichlorobenzoyl)-4-(2,6-dimethoxy-4-ethoxymethylphenyl)-L-phenylalanine ethyl ester (1) To a mixture of L-tyrosine ethyl ester hydrochloride (55.08 g) and $NaHCO_3$ (22.52 g) in $CH_2Cl_2/H_2O$ (280 ml/280 ml) was added di-tert-butyl bicarbonate (56.82 g) portionwise. The mixture was stirred for 2 hours at room temperature and diluted with AcOEt. The organic layer was washed with $H_2O$, dried ($Na_2SO_4$) and evaporated. The residue was recrystallized from a mixture of diethyl ether and hexane to yield N-(tert-butoxycarbonyl)-L-tyrosine ethyl ester (62.71 g). mp. 87-88° C.; MS (APCI) m/z 327 (M+$NH_4$), 310 (M+H).

(2) Pyridine (48 ml) was added to a solution of the product obtained above (61.639) in $CH_2Cl_2$ (1800 ml) under argon. The solution was cooled to −35 to −30° C. and triflic anhydride (35 ml) was added dropwise with stirring. After the addition, the mixture was stirred at −30 to −20° C. for 2 hours. Ice-water was added to the mixture and the organic layer was separated, washed with 5% aqueous citric acid, $H_2O$, and brine. The resulting $CH_2Cl_2$ solution was dried ($Na_2SO_4$) and evaporated. The residue was purified by column chromatography (silica gel; eluent: n-hexane/EtOAc 4:1) to yield N-(tert-butoxycarbonyl)-O-(trifluoromethanesulfonyl)-L-tyrosine ethyl ester (87.94 g). mp. 47-49° C.; IR (Nujol) 3390, 1737, 1691 cm$^{-1}$; MS (APCI) m/z (M+$NH_4$).

(3) To a mixture of the product obtained above (76.51 g) and 2,6-dimethoxy-4-hydroxymethylbenzene boronic acid (62.27 g) in DMF (350 ml) was added Et$_3$N (41 g) and degassed with argon. Pd(PPh$_3$)$_4$ (19.5 g) was added to the mixture and stirred at 80-90° C. under argon for 1 hour. The mixture was cooled, diluted with AcOEt and H$_2$O, filtered through Celite and washed with AcOEt. The filtrate was diluted with H$_2$O and separated. The organic layer was washed with H$_2$O and brine, dried (Na$_2$SO$_4$), treated with charcoal and evaporated. The residue was purified by column chromatography (silica gel; eluent: n-hexane/EtOAc 3:2 to 2:3) and recrystallized from iso-PrOH to yield N-(tert-butoxycarbonyl)-4-(2,6-dimethoxy-4-hydroxymethylphenyl)-L-phenylalanine ethyl ester (69.4 g). mp. 142-143° C.; IR (Nujol) 3507, 3323, 1731, 1689, 1606 cm$^{-1}$; MS (APCI) m/z 477 (M+NH$_4$)

(4) To a solution of the product obtained above (10.0 g) in dioxane (50 ml) was added 4N HCl-dioxane (50 ml) at 0° C. and the mixture was stirred at room temperature for 2 hours. The mixture was diluted with diethyl ether. The resulting precipitate was collected by filtration and washed with diethyl ether to yield 4-(2,6-dimethoxy-4-hydroxymethylphenyl)-L-phenylalanine ethyl ester hydrochloride (8.26 g). IR(Nujol) 3321, 1735 cm$^{-1}$; MS (APCI+Q1MS) m/z 360 (M+H)

(5) To a mixture of the product obtained above (1.5 g) in AcOEt/H$_2$O (60 ml/60 ml) containing NaHCO$_3$ (955 mg) was added 2,6-dichlorobenzoyl chloride (0.6 ml) at 0° C. and the mixture was stirred at 0° C. for 0.5 hour. The mixture was diluted with AcOEt, H$_2$O and a small amount of CH$_2$Cl$_2$. The organic layer was washed with brine, dried (Na$_2$SO$_4$) and evaporated. The residue was crystallized to yield N-(2,6-dichlorobenzoyl)-4-(2,6-dimethoxy-4-hydroxymethylphenyl)-L-phenylalanine ethyl ester (1.93 g). mp. 121° C.; IR (Nujol) 3249, 1725, 1641 cm$^{-1}$; MS (APCI+Q1MS) m/z 532 (M+H).

(6) To a solution of the product obtained above (508 mg) in CH$_2$Cl$_2$ (10 ml) was added MnO$_2$ (976 mg). The mixture was stirred at room temperature for 2.5 hours and refluxed for 14 hours. The mixture was cooled, filtered through Celite and washed with CH$_2$Cl$_2$. The filtrate was evaporated to yield N-(2,6-dichlorobenzoyl)-4-(2,6-dimethoxy-4-formylphenyl)-L-phenylalanine ethyl ester (352 mg). IR (Nujol) 1734, 1691, 1655 cm$^{-1}$; MS (APCI) m/z 530 (M+H).

(7) To a mixture of the product obtained above (345 mg) in EtOH (4 ml) containing Et$_3$SiH (226 mg) was added conc. H$_2$SO$_4$ (0.5 ml). After stirring at room temperature for 18 hours, the mixture was treated with a mixture of AcOEt and H$_2$O. The organic layer was sequentially washed with H$_2$O and brine, dried (MgSO$_4$) and evaporated. The residue was purified by column chromatography (silica gel; eluent: n-hexane/AcOEt 2:1) and crystallized from a mixture of diisopropyl ether and iso-propanol to yield the title compound (254 mg). mp. 91-94° C.; IR (Nujol) 3290, 1729, 1652, 1463, 1123 cm$^{-1}$; MS (APCI+Q1MS) m/z 560 (M+H).

Example 2

N-(2,6-Dichlorobenzoyl)-4-(2,6-dimethoxy-4-ethoxymethylphenyl)-L-phenylalanine methyl ester (1) N-(tert-butoxycarbonyl)-L-tyrosine methyl ester (3.34 g) was obtained in a similar manner as described in Example 1-(1) from L-tyrosine methyl ester hydrochloride (2.69 g). mp. 105-106° C.; IR (Nujol) 3415, 3321, 1761, 1691 cm$^{-1}$; MS (APCI+Q1MS) m/z 313 (M+NH$_4$), 296 (M+H)

(2) The product obtained above (3.3 g) was converted into N-(tert-butoxycarbonyl)-O-(trifluoromethanesulfonyl)-L-tyrosine methyl ester (4.62 g) in a similar manner as described in Example 1-(2). IR (Neat) 3366, 1747, 1715 cm$^{-1}$; MS (APCI+Q1MS) m/z 445 (M+NH$_4$)

(3) The product obtained above (4.56 g) was converted into N-(tert-butoxycarbonyl)-4-(2,6-dimethoxy-4-hydroxymethylphenyl)-L-phenylalanine methyl ester (3.21 g) in a similar manner as described in Example 1-(3). mp. 100° C.; IR (Nujol) 3360, 1739, 1683, 1661 cm$^{-1}$; MS (APCI) m/z 463 (M+NH$_4$).

(4) The product obtained above (3.19 g) was converted into 4-(2,6-dimethoxy-4-hydroxymethylphenyl)-L-phenylalanine methyl ester hydrochloride (2.45 g) in a similar manner as described in Example 1-(4). mp. 211-213° C. (dec.); IR (Nujol) 3301, 1739 cm$^{-1}$; MS (APCI+Q1MS) m/z 346 (M+H).

(5) The product obtained above (1.08 g) was converted into N-(2,6-dichlorobenzoyl)-4-(2,6-dimethoxy-4-hydroxymethylphenyl)-L-phenylalanine methyl ester (874 mg) in a similar manner as described in Example 1-(5). mp. 116-120° C.; IR (Nujol) 3230, 3069, 1749, 1732, 1641 cm$^{-1}$; MS (APCI+Q1MS) m/z 518 (M+H).

(6) To a mixture of the product obtained above (937 mg) in dioxane (10 ml) containing NaHCO$_3$ (304 mg) was added a solution of PBr$_3$ (680 mg) in dioxane (2 ml) portionwise at room temperature. After stirring for 20 minutes, the mixture was quenched with ice and extracted with AcOEt. The organic layer was sequentially washed with H$_2$O and brine, dried (MgSO$_4$) and evaporated. The residue was purified by column chromatography (silica gel; eluent: AcOEt/CHCl$_3$ 1:10) to yield N-(2,6-dichlorobenzoyl)-4-(4-bromomethyl-2,6-dimethoxyphenyl)-L-phenylalanine methyl ester (598 mg). MS (APCI+Q1MS) m/z 584, 582, 580 (M+H).

(7) A mixture of the product obtained above (571 mg) in EtOH (20 ml) containing AgO (659 mg) was sonicated at room temperature for 7 hours. The mixture was filtered through Celite and washed with EtOH. The filtrate was evaporated and the residue was purified by column chromatography (silica gel; eluent: AcOEt/CHCl$_3$ 1:20) to yield the title compound (318 mg). MS (APCI+Q1MS) m/z 546 (M+H).

Example 3

N-(2,6-Dichlorobenzoyl)-4-(2,6-dimethoxy-4-ethoxmethylphenyl)-L-phenylalanine

To a solution of the compound of Example 1 (207 mg) in THF/H$_2$O (8 ml/2 ml) was added LiOH (30 mg) at 5° C. The mixture was stirred at 5° C. for 20 hours, quenched with 6N HCl (1 ml) and extracted with AcOEt. The organic layer was washed with H$_2$O and brine, dried (MgSO$_4$) and evaporated. The residue was recrystallized from a mixture of MeOH, diethyl ether and hexane to yield the title compound (147 mg). The compound of Example 2 (301 mg) was also hydrolyzed in a similar manner to give the title compound (238 mg) mp. 196-198° C.; IR (Nujol) 3300, 3270, 1705, 1651, 1462, 1126 cm$^{-1}$; MS (ESI-Q1MS) m/z 530 (M–H).

Example 4

N-(2,6-Dichlorobenzoyl)-4-(2,6-dimethoxy-4-methoxymethylphenyl)-L-phenylalanine ethyl ester To a mixture of the compound from Example 1-(5) or Reference Example 3-(3) (304 mg) in CH$_3$CN (30 ml) containing Ag$_2$O (868 mg) was added MeI (871 mg). The mixture was stirred at room temperature for 18.5 hours and then sonicated at 50° C. for 5 hours. The mixture was filtered through Celite and the filtrate was evaporated. The residue was purified by column chromatography (silica gel; eluent: AcOEt/n-hexane 1:2) to yield the title compound (222 mg). IR (Neat+CHCl$_3$) 3285, 1736, 1663 cm$^{-1}$; MS (APCI+Q1MS) m/z 546 (M+H).

Example 5

N-(2,6-Dichlorobenzoyl)-4-(2,6-dimethoxy-4-methoxymethylphenyl)-L-phenylalanine

The product obtained in Example 4 (210 mg) was converted into the title compound (139 mg) in a similar manner as described in Example 3. mp. 232-235° C.; IR (Nujol) 3336, 1717, 1685 cm$^{-1}$; MS (ESI–Q1MS) m/z 516 (M–H).

Example 6

N-(2,6-Dichlorobenzoyl)-4-(2,6-dimethoxy-4-n-propoxymethylphenyl)-L-phenylalanine ethyl ester (1) To a solution of the product obtained in Example 1-(5) or Reference Example 3-(3) (3.0 g) in CH$_2$Cl$_2$ (80 ml) containing PPh$_3$ (1.77 g) was added CBr$_4$ (2.8 g) at 0° C. The mixture was stirred at room temperature for 3 hours and evaporated. The residue was purified by column chromatography (silica gel; eluent: AcOEt/n-hexane 1:1) to yield N-(2,6-dichlorobenzoyl)-4-(2,6-dimethoxy-4-bromomethylphenyl)-L-phenylalanine ethyl ester (3.15 g). IR (Nujol) 1731, 1654; cm$^{-1}$; MS (APCI) m/z 596 (M+H)

(2) A mixture of the product obtained above (304 mg) in n-PrOH (12 ml) containing AgO (515 mg) was sonicated at 45° C. under argon for 28 hours. The mixture was filtered through Celite and the filtrate was evaporated. The residue was purified by column chromatography (silica gel; eluent: n-hexane/AcOEt 3:1) to yield the title compound (258 mg). IR (Nujol) 1733, 1655 cm$^{-1}$; MS (APCI) m/z 574 (M+H)

Example 7

N-(2,6-Dichlorobenzoyl)-4-(2,6-dimethoxy-4-n-propoxymethylphenyl)-L-phenylalanine The product obtained in Example 6 (150 mg) was converted into the title compound (142 mg) in a similar manner as described in Example 3. mp. 183-186° C.; IR (Nujol) 1719, 1684 cm$^{-1}$; MS (APCI) m/z 544 (M–H)

Example 8

N-(2,6-Dichlorobenzoyl)-4-(2,6-dimethoxy-4-isopropoxymethylphenyl)-L-phenylalanine ethyl ester The product obtained in Example 6-(1) (231 mg) was converted into the title compound (179 mg) in a similar manner as described in Example 6-(2) using iso-PrOH instead of n-PrOH. IR (Nujol) 3270, 1731, 1658 cm$^{-1}$; MS (APCI) m/z 574 (M+H).

Example 9

N-(2,6-Dichlorobenzoyl)-4-(2,6-dimethoxy-4-isopropoxymethylphenyl)-L-phenylalanine The product obtained in Example 8 (122 mg) was hydrolyzed in a similar manner as described in Example 3 to give the title compound (117 mg). IR (Nujol) 3341, 3070, 1718, 1681 cm$^{-1}$; MS (ESI) m/z 544 (M–H).

Example 10

N-(2,6-Difluorobenzoyl)-4-(2,6-dimethoxy-4-ethoxymethylphenyl)-L-phenylalanine ethyl ester (1) The product obtained in Example 1-(4) (2.1 g) was acylated with 2,6-difluorobenzoyl chloride in a similar manner as described in Example 1-(5) to give N-(2,6-difluorobenzoyl)-4-(2,6-dimethoxy-4-hydroxymethylphenyl)-L-phenylalanine ethyl ester (2.75 g). mp. 70-72° C.; IR (Nujol) 3400, 3263, 1735, 1654, 1624 cm$^{-1}$; MS (APCI) m/z 500 (M+H).

(2) To a solution of the product obtained above (1.72 g) in DMSO (20 ml) were added Et$_3$N (4.8 ml) and SO$_3$·pyridine (5.6 g) successively at room temperature. The whole mixture was stirred at room temperature for 25 minutes. The reaction mixture was poured into ice-water, and then the mixture was extracted with EtOAc. The organic layer was sequentially washed with 5% aqueous HCl, H$_2$O and brine, dried (Na$_2$SO$_4$) and then evaporated. The residue was purified by column chromatography (silica gel; eluent: n-hexane/EtOAc 5:1 to 1:1) to yield N-(2,6-difluorobenzoyl)-4-(2,6-dimethoxy-4-formylphenyl)-L-phenylalanine ethyl ester (1.54 g). mp. 114-116° C.; IR (Nujol) 3332, 1735, 1695, 1657, 1644, 1623 cm$^{-1}$; MS (APCI) m/z 498 (M+H).

(3) The product obtained above (716 mg) was converted into the title compound (428 mg) in a similar manner as described in Example 1-(7). mp. 87-89° C.; IR (Neat+CHCl$_3$) 3300, 1739, 1668 cm$^{-1}$; MS (APCI) m/I 528 (M+H).

Example 11

N-(2,6-Difluorobenzoyl)-4-(2,6-dimethoxy-4-ethoxymethylphenyl)-L-phenylalanine methyl ester (1) The product obtained in Example 2-(4) (1.00 g) was acylated with 2,6-difluorobenzoyl chloride to give N-(2,6-difluorobenzoyl)-4-(2,6-dimethoxy-4-hydroxymethylphenyl)-L-phenylalanine methyl ester (873 mg) in a similar manner as described in Example 1-(5). IR (Nujol) 3257, 1743, 1655, 1624 cm$^{-1}$; MS (APCI+Q1MS) m/z 503 (M+NH$_4$), 486 (M+H).

(2) The product obtained above (860 mg) was converted into the title compound (220 mg) in a similar manner as described in Example 2-(6) and (7).

Example 12

N-(2,6-Difluorobenzoyl)-4-(2,6-dimethoxy-4-ethoxymethylphenyl)-L-phenylalanine

The product obtained in Example 10 (200 mg) was hydrolyzed in a similar manner as described in Example 3 to give the title compound (160 mg). The product obtained in Example 11 (220 mg) was also hydrolyzed in a similar manner as described in Example 3 to give the title compound (167 mg). mp. 156-158° C.; IR (Nujol) 1735, 1655 cm$^{-1}$; MS (ESI) m/I 498 (M–H).

Example 13

N-(2,6-Difluorobenzoyl)-4-(2,6-dimethoxy-4-methoxymethylphenyl)-L-phenylalanine ethyl ester (1) The product (1.41 g) obtained in Example 10-(1) or Reference Example 4-(3) was converted into N-(2,6-difluorobenzoyl)-4-(2,6-dimethoxy-4-bromomethylphenyl)-L-phenylalanine ethyl ester (1.22 g) in a similar manner as described in Example 6-(1). IR (Nujol) 3317, 1740, 1653, 1623 cm$^{-1}$; MS (APCI) m/z 564 (M+H).

(2) The product obtained above (231 mg) was converted into the title compound (96 mg) in a similar manner as described in Example 6-(2) using MeOH instead of n-PrOH. IR (Nujol) 3347, 1754, 1655, 1626 cm$^{-1}$; MS (APCI+Q1MS) m/z 514 (M+H).

Example 14

N-(2,6-Difluorobenzoyl)-4-(2,6-dimethoxy-4-methoxymethylphenyl)-L-phenylalanine The product obtained in Example 13 (96 mg) was hydrolyzed in a similar manner as described in Example 3 to give the title compound (62 mg). IR (Nujol) 3303, 3275, 1724, 1709, 1655, 1626 cm$^{-1}$; MS (ESI–Q1MS) m/z 484 (M–H).

Example 15

N-(2,6-Difluorobenzoyl)-4-(2,6-dimethoxy-4-n-propoxymethylphenyl)-L-phenylalanine ethyl ester The product obtained in Example 13-(1) was converted into the title compound in a similar manner as described in Example 6-(2) IR (Neat) 3302, 1739, 1674, 1624 cm$^{-1}$; MS (APCI) m/z 542 (M+H).

Example 16

N-(2,6-Difluorobenzoyl)-4-(2,6-dimethoxy-4-isopropoxymethylphenyl)-L-phenylalanine ethyl ester The product obtained in Example 13-(1) was converted into the title compound in a similar manner as described in Example 6-(2) using iso-PrOH instead of n-PrOH. IR (Nujol) 3332, 1756, 1653, 1625 cm$^{-1}$; MS (APCI+Q1MS) m/z 542 (M+H).

Example 17

N-(2,6-Difluorobenzoyl)-4-(2,6-dimethoxy-4-n-propoxymethylphenyl)-L-phenylalanine The product obtained in Example 15 was hydrolyzed in a similar manner as described in Example 3 to give the title compound. IR (Nujol) 1735, 1660, 1624 cm$^{-1}$; MS (ESI) m/z 512 (M–H).

Example 18

N-(2,6-Difluorobenzoyl)-4-(2,6-dimethoxy-4-isopropoxymethylphenyl)-L-phenylalanine The product obtained in Example 16 was hydrolyzed in a similar manner as described in Example 3 to give the title compound. IR (Nujol) 1735, 1655, 1624 cm$^{-1}$; MS (ESI–Q1MS) m/z 512 (M–H).

Example 19

N-(2-Chloro-6-fluorobenzoyl)-4-(2,6-dimethoxy-4-ethoxymethylphenyl)-L-phenylalanine ethyl ester (1) To a solution of the product obtained in Example 1-(4) (863 mg) and 2-chloro-6-fluorobenzoic acid (456 mg) in DMF (15 ml) were added EDC.HCl (549 mg), HOBt (383 mg) and 4-methylmorpholine (0.48 ml) successively at room temperature. The mixture was stirred at room temperature for 14 hours and diluted with H$_2$O. The mixture was extracted with AcOEt and the organic layer was sequentially washed with saturated aqueous NaHCO$_3$, H$_2$O and brine. The resulting organic layer was dried (Na$_2$SO$_4$) and evaporated. The residue was purified by column chromatography (silica gel; eluent: n-hexane/AcOEt 1:1) to yield N-(2-chloro-6-fluorobenzoyl)-4-(2,6-dimethoxy-4-hydroxymethylphenyl)-L-phenylalanine ethyl ester (950 mg). mp. 101-104° C.; IR (Nujol) 2921, 2853, 1733, 1652, 1605 cm$^{-1}$; MS (APCI) m/z 516 (M+H)

(2) The product obtained above (630 mg) was oxidized in a similar manner as described in Example 1-(6) to give N-(2-chloro-6-fluorobenzoyl)-4-(2,6-dimethoxy-4-formylphenyl)-L-phenylalanine ethyl ester (466 mg). IR (Nujol) 3279, 1735, 1691, 1657 cm$^{-1}$; MS (APCI+Q1MS) m/z 514 (M+H).

(3) The product obtained above (466 mg) was converted into the title compound (454 mg) in a similar manner as described in Example 1-(7). IR (Neat+CHCl$_3$) 3289, 1737, 1663, 1605 cm$^1$; MS (APCI) m/z 544 (M+H).

Example 20

N-(2-Chloro-6-fluorobenzoyl)-4-(2,6-dimethoxy-4-ethoxymethylphenyl)-L-phenylalanine To a solution of the product obtained in Example 19 (210 mg) in THF (5 ml) were added 0.5N LiOH (1.54 ml) and 3% H$_2$O$_2$ (65 μl) at 5° C. The mixture was stirred at 5° C. for 14 hours and acidified with 1 N HCl. The mixture was concentrated, diluted with H$_2$O and the resulting precipitate was collected by filtration and washed with H$_2$O to yield the title compound (171 mg). mp. 182-184° C.; IR (Nujol) 3295, 1729, 1711, 1653 cm$^{-1}$; MS (ESI) m/z 514 (M–H)

Example 21

N-(2-Chloro-6-fluorobenzoyl)-4-(2,6-dimethoxy-4-methoxymethylphenyl)-L-phenylalanine methyl ester (1) The product obtained in Example 2-(4) (49 g) was acylated with 2-chloro-6-fluorobenzoic acid to give N-(2-chloro-6-fluorobenzoyl)-4-(2,6-dimethoxy-4-hydroxymethylphenyl)-L-phenylalanine methyl ester (58 g) in a similar manner as described in Example 19-(1). IR (Nujol) 1735, 1651 cm$^{-1}$; MS (APCI) m/z 519 (M+NH$_4$).

(2) The product obtained above (58 g) was oxidized in a similar manner as described in Example 1-(6) to give N-(2-chloro-6-fluorobenzoyl)-4-(2,6-dimethoxy-4-formylphenyl)-L-phenylalanine methyl ester (45.8 g). IR (Nujol) 3275, 1743, 1691 cm$^{-1}$; MS (APCI+Q1MS) m/z 500 (M+H)

(3) The product obtained above (2.0 g) was converted into the title compound (1.4 g) in a similar manner as described in Example 1-(7) using MeOH instead of EtOH. IR (Neat+CHCl$_3$) 3285, 1745, 1665, 1605 cm$^{-1}$; MS (APCI+Q1MS) m/z 533 (M+NH$_4$), 516 (M+H).

Example 22

N-(2-Chloro-6-fluorobenzoyl)-4-(2,6-dimethoxy-4-methoxymethylphenyl)-L-phenylalanine ethyl ester (1) The product obtained in Example 19-(1) or Reference Example 5-(3) (3.29 g) was converted into N-(2-chloro-6-fluorobenzoyl)-4-(2,6-dimethoxy-4-bromomethylphenyl)-L-phenylalanine ethyl ester (2.91 g) in a similar manner as described in Example 6-(1). IR (Neat+$CHCl_3$) 3315, 1735, 1662, 1603 $cm^{-1}$; MS (APCI) m/z 582, 580, 578 (M+H).

(2) The product obtained above (250 mg) was converted in a similar manner as described in Example 2-(7) using MeOH instead of EtOH into the title compound (190 mg). IR (Nujol) 1736, 1659 $cm^{-1}$; MS (APCI) m/z 530 (M+H).

Example 23

N-(2-Chloro-6-fluorobenzoyl)-4-(2,6-dimethoxy-4-methoxymethylphenyl)-L-phenylalanine The product obtained in Example 22 (130 mg) was hydrolyzed in a similar manner as described in Example 3 to give the title compound (100 mg). mp. 170-175° C.; IR (Nujol) 1720, 1680 $cm^{-1}$; MS (ESI) m/z 500 (M−H).

The product obtained in Example 21 (27.9 g) was also converted into the title compound (25.3 g) in a similar manner.

Example 24

N-(2-Chloro-6-fluorobenzoyl)-4-(2,6-dimethoxy-4-n-propoxymethylphenyl)-L-phenylalanine ethyl ester The product obtained in Example 22-(1) was converted into the title compound in a similar manner as described in Example 2-(7) using n-PrOH instead of EtOH.

IR (Neat+$CHCl_3$) 1737, 1667 $cm^{-1}$; MS (APCI) m/z 558 (M+H).

Example 25

N-(2-Chloro-6-fluorobenzoyl)-4-(2,6-dimethoxy-4-iso-propoxymethylphenyl)-L-phenylalanine ethyl ester The product obtained in Example 22-(1) was converted into the title compound in a similar manner as described in Example 2-(7) using iso-PrOH instead of EtOH.

IR (Neat+$CHCl_3$) 3305, 1737, 1665, 1605 $cm^{-1}$; MS (APCI) m/z 558 (M+H).

Example 26

N-(2-Chloro-6-fluorobenzoyl)-4-(2,6-dimethoxy-4-n-propoxymethylphenyl)-L-phenylalanine The product obtained in Example 24 was hydrolyzed in a similar manner as described in Example 3 to give the title compound. IR (Nujol) 1713, 1654 $cm^{-1}$; MS (APCI) m/z 528 (M−H)

Example 27

N-(2-Chloro-6-fluorobenzoyl)-4-(2,6-dimethoxy-4-iso-propoxymethylphenyl)-L-phenylalanine The product obtained in Example 25 was hydrolyzed in a similar manner as described in Example 3 to give the title compound. IR (Neat+$CHCl_3$) 3400, 3280, 1737, 1660, 1605 $cm^{-1}$; MS (ESI) m/z 528 (M−H).

Example 28

N-(2,6-Dichlorobenzoyl)-4-[2,6-dimethoxy-4-(2-ethoxyethyl)phenyl]-L-phenylalanine tert-butyl ester (1) L-Tyrosine tert-butyl ester (2.5 g) was acylated in a similar manner as described in Example 1-(5) to give N-(2,6-dichlorobenzoyl)-L-tyrosine tert-butyl ester (4.3 g). mp. 177-178° C.; IR (Nujol) 1721, 1652 $cm^{-1}$; MS (APCI) m/z 427 (M+$NH_4$), 410 (M+H).

(2) The product obtained above (4.3 g) was converted in a similar manner as described in Example 1-(2) into N-(2,6-dichlorobenzoyl)-O-(trifluoromethanesulfonyl)-L-tyrosine tert-butyl ester (5.6 g). mp. 92-93° C.; IR (Nujol) 1716, 1643 $cm^{-1}$; MS (APCI) m/z 559 (M+$NH_4$).

(3) To a degassed suspension of the product obtained above (4.07 g), 2,6-dimethoxy-4-(2-hydroxyethyl)benzene boronic acid (2.71 g, crude) and $Et_3N$ (2.27 g) in DMF (100 ml) was added Pd($PPh_3$)$_4$ (866 mg). The mixture was heated at 80-90° C. for 2 hours under argon. The resulting mixture was diluted with AcOEt, washed with $H_2O$ and filtered through Celite. The organic layer was separated, dried ($MgSO_4$) and evaporated. The residue was purified by column chromatography (basic silica gel (Chromatorex-NH, Fuji Silysia Chem. LTD); eluent: AcOEt; and then silica gel; eluent: AcOEt/n-hexane 3:2 to 2:1) and recrystallized from diethyl ether to yield N-(2,6-dichlorobenzoyl)-4-[2,6-dimethoxy-4-(2-hydroxyethyl)phenyl]-L-phenylalanine tert-butyl ester (2.5 g). mp. 96-98° C.; IR (Nujol) 1727, 1645 $cm^{-1}$; MS (APCI) m/z 591 (M+$NH_4$).

(4) The product obtained above (254 mg) was alkylated with EtI in a similar manner as described in Example 4 to give the title compound (116 mg). IR (Neat+$CHCl_3$) 3301, 1730, 1669 $cm^{-1}$; MS (APCI) m/z 619 (M+$NH_4$).

Example 29

N-(2,6-Dichlorobenzoyl)-4-[2,6-dimethoxy-4-(2-ethoxyethyl)phenyl]-L-phenylalanine To a solution of the product obtained in Example 28 (109 mg) in $CH_2Cl_2$ (2 ml) was added 4N HCl-dioxane (3 ml) at room temperature. The mixture was stirred at room temperature for 3 days and evaporated. The residue was purified by column chromatography (silica gel; eluent: n-hexane/AcOEt 1:1) to yield the title compound (88 mg). IR (Nujol) 3320, 3067, 1736, 1715, 1683 $cm^{-1}$; MS (ESI) m/z 544 (M−H).

Example 30

N-(2,6-Difluorobenzoyl)-4-[2,6-dimethoxy-4-(2-ethoxyethyl)phenyl]-L-phenylalanine tert-butyl ester (1) L-tyrosine tert-butyl ester (10.0 g) was acylated with 2,6-difluorobenzoyl chloride in a similar manner as described Example 1-(5) to give N-(2,6-difluorobenzoyl)-L-tyrosine tert-butyl ester (15.9 g). mp. 145-148° C.; IR (Nujol) 1728, 1638 cm$^{-1}$; MS (APCI) m/z 395 (M+NH$_4$), 378 (M+H).

(2) The product obtained above (15.9 g) was converted in a similar manner as described in Example 1-(2) into N-(2,6-difluorobenzoyl)-O-(trifluoromethanesulfonyl)-L-tyrosine tert-butyl ester (21.04 g). IR (Neat+CHCl$_3$) 1732, 1658 cm$^{-1}$; MS (APCI) m/z 527 (M+NH$_4$).

(3) The product above (5.61 g) was converted into N-(2,6-difluorobenzoyl)-4-[2,6-dimethoxy-4-(2-hydroxyethyl)phenyl]-L-phenylalanine tert-butyl ester (3.54 g) in a similar manner as described in Example 28-(3). IR (Neat+CHCl$_3$) 3307, 1731, 1660 cm$^{-1}$; MS (APCI) m/z 559 (M+NH$_4$), 542 (M+H).

(4) The product obtained above (250 mg) was alkylated with EtI in a similar manner as described in Example 4 to give the title compound (230 mg). IR (Neat+CHCl$_3$) 1731, 1675 cm$^{-1}$; MS (APCI) m/z 588 (M+NH$_4$), 570 (M+H).

Example 31

N-(2,6-Difluorobenzoyl)-4-[2,6-dimethoxy-4-(2-ethoxyethyl)phenyl]-L-phenylalanine The product obtained in Example 30 (200 mg) was hydrolyzed in a similar manner as described in Example 29 to give the title compound (161 mg). mp. 63-70° C.; IR (Nujol) 1737, 1660, 1624 cm$^{-1}$; MS (APCI) m/z 512 (M−H).

Example 32

N-(2,6-Difluorobenzoyl)-4-[2,6-dimethoxy-4-(2-methoxyethyl)phenyl]-L-phenylalanine ethyl ester (1) The product obtained in Example 1-(2) (43.83 g) was converted in a similar manner as described in Example 28-(3) into N-(tert-butoxycarbonyl)-4-[2,6-dimethoxy-4-(2-hydroxyethyl)phenyl]-L-phenylalanine ethyl ester (38.03 g). mp. 112-114° C. IR (Nujol) 3487, 3327, 1729, 1688, 1607 cm$^{-1}$; MS (APCI) m/z 491 (M+NH$_4$).

(2) The product obtained above (3.04 g) was converted in a similar manner as described in Example 1-(4) into 4-[2,6-dimethoxy-4-(2-hydroxyethyl) phenyl]-L-phenylalanine ethyl ester hydrochloride (2.57 g). IR (Nujol) 3400, 1730 cm$^{-1}$; MS (APCI) m/z 374 (M+H).

(3) The product obtained above (2.57 g) was acylated with 2,6-difluorobenzoyl chloride in a similar manner as described in Example 1-(5) to give N-(2,6-difluorobenzoyl)-4-[2,6-dimethoxy-4-(2-hydroxyethyl)phenyl]-L-phenylalanine ethyl ester (2.35 g). mp. 115-117° C.; IR (Nujol) 3568, 3355, 1753, 1655, 1627 cm$^{-1}$; MS (APCI) m/z 514 (M+H).

(4) The product obtained above (329 mg) was alkylated in a similar manner as described in Example 4 to give the title compound (294 mg). IR (Nujol) 3341, 1755, 1655, 1625 cm$^{-1}$; MS (APCI) m/z 528 (M+H)

Example 33

N-(2,6-Difluorobenzoyl)-4-[2,6-dimethoxy-4-(2-methoxyethyl) phenyl]-L-phenylalanine The product obtained in Example 32 (187 mg) was hydrolyzed in a similar manner as described in Example 3 to give the title compound (143 mg). IR (Neat+CHCl$_3$) 1739, 1667 cm$^{-1}$; MS (APCI) m/z 498 (M−H).

Example 34

N-(2,6-Dichlorobenzoyl)-4-(2,6-dimethoxy-4-ethoxymethylphenyl)-L-phenylalanine ethyl ester The title compound in Example 1 was also obtained by the following alternative route.

(1) To a solution of the product obtained in Example 1-(5) or Reference Example 3-(3) (3.00 g) in CH$_2$CO$_2$ (50 ml) were added methanesulfonyl chloride (0.523 ml) and Et$_3$N (1.02 ml) at −5° C. The mixture was stirred for 1 hour at −10° C. to 0° C., diluted with H$_2$O and extracted with CHCl$_2$ twice. The organic layer was washed with brine, dried (Na$_2$SO$_4$) and evaporated. The residue was triturated with AcOEt-hexane and collected by filtration to yield N-(2,6-dichlorobenzoyl)-4-(2,6-dimethoxy-4-methanesulfonyloxymethylphenyl)-L-phenylalanine ethyl ester (3.34 g). mp. 109° C.; IR (Nujol) 3273, 2923, 2854, 1733, 1655, 1583, 1463 cm$^{-1}$; MS (APCI) m/z 610 (M+H).

(2) A suspension of the product obtained above (101 mg) in EtOH (2 ml) was stirred at 90° C. for 45 minutes. The mixture was cooled, diluted with H$_2$O and extracted with AcOEt twice. The organic layer was washed with brine, dried (Na$_2$SO$_4$) and evaporated. The residue was purified by column chromatography (silica gel; eluent: n-hexane/AcOEt 2:1) to yield the title compound (89 mg).

Example 35

N-(2,6-Dichlorobenzoyl)-4-(2,6-dimethoxy-4-ethoxymethylphenyl)-L-phenylalanine ethyl ester The title compound in Example 1 was also obtained by the following alternative route.

To a suspension of the product obtained in Example 1-(5) or Reference Example 3-(3) (532 mg) in EtOH (10 ml) was added sulfuric acid (1 ml). The mixture was stirred under reflux for 24 hours. The resulting mixture was cooled, diluted with H$_2$O and extracted with AcOEt. The organic layer was washed with H$_2$O, brine, dried (Na$_2$SO$_4$) and evaporated. The residue was purified by column chromatography (silica gel; eluent: n-hexane/AcOEt 2:1) to yield the title compound (476 mg).

Example 36

N-(2,6-Difluorobenzoyl)-4-(2,6-dimethoxy-4-ethoxymethylphenyl)-L-phenylalanine ethyl ester The title compound in Example 10 was also obtained by the following alternative route.

(1) The product obtained in Example 10-(1) or Reference Example 4-(3) (73.4 g) was sulfonylated in a similar manner as described in Example 34-(1) to give N-(2,6-difluorobenzoyl)-4-(2,6-dimethoxy-4-methanesulfonyloxymethylphenyl)-L-phenylalanine ethyl ester (77.7 g). mp. 125-126° C.; IR (Nujol) 3335, 2922, 2853, 1756, 1735, 1653, 1625, 1583, 1525, 1464 cm$^{-1}$; MS (APCI) m/z 595 (M+N$_4$).

(2) The product obtained above (77.7 g) was converted into the title compound (70.5 g) in a similar manner as described in Example 34-(2).

Example 37

N-(2-Chloro-6-fluorobenzoyl)-4-(2,6-dimethoxy-4-ethoxymethylphenyl)-L-phenylalanine ethyl ester The title compound in Example 19 was also obtained by the following alternative route.

(1) The product obtained in Example 19-(1) or Reference Example 5-(3) (12.4 g) was sulfonylated in a similar manner as described in Example 34-(1) to give N-(2-chloro-6-fluorobenzoyl)-4-(2,6-dimethoxy-4-methanesulfonyloxymethylphenyl)-L-phenylalanine ethyl ester (14.0 g). mp. 104-107° C.; IR (Nujol) 3286, 1734, 1655, 1605, 1583, 1541, 1460 cm$^{-1}$; MS (APCI) m/z 611 (M+NH$_4$).

(2) The product obtained above (14.0 g) was converted into the title compound (13.0 g) in a similar manner as described in Example 34-(2).

Reference Example 1

2,6-Dimethoxy-4-hydroxymethylbenzene boronic acid

To a solution of 3,5-dimethoxybenzyl alcohol (80 g) in THF (1900 ml) was added n-BuLi (1.6 M in n-hexane, 750 ml) portionwise at −50° C. for 0.5 hour under argon. The mixture was warmed up to room temperature for 2 hours and cooled again to −60° C. To the mixture was added (MeO)$_3$B (200 ml). The resulting mixture was warmed to room temperature and stirred over night. To the reaction mixture was added a solution of citric acid (300 g) in H$_2$O (1200 ml) portionwise at 0° C. The aqueous layer was separated, saturated with NaCl and extracted with AcOEt. The combined AcOEt extract was dried (Na$_2$SO$_4$) and evaporated. The crystalline residue was triturated with AcOEt and collected by filtration to yield the title compound (75.1 g). mp. 92-98° C.; IR (Nujol) 3460, 3408, 3218, 1613, 1578, 1288, 1231, 1123, 1055, 960, 779 cm$^1$; MS (APCI) m/z 230 (M+NH$_4$).

Reference Example 2

2,6-Dimethoxy-4-(2-hydroxyethyl)benzene boronic acid (1) To a mixture of LiAlH$_4$ (1.05 g) in dioxane (100 ml) was added a solution of 3,5-dimethoxyphenyl acetic acid (5.32 g) in dioxane (20 ml) portionwise at 0° C. The mixture was stirred at room temperature for 0.5 hour and at 50° C. for 2 hours. The mixture was quenched with conc. NH$_4$OH and filtered through Celite. The filtrate was evaporated to yield 3,5-dimethoxyphenethyl alcohol (5.1 g). IR (Neat) 3400, 1600 cm$^{-1}$; MS (GC–EI) 182 (M$^+$), 151 (M—MeO).

(2) The product obtained above (27.16 g) was converted in a similar manner as described in Reference Example 1 into the title compound (39.1 g).

Reference Example 3

N-(2,6-Dichlorobenzoyl)-4-(2,6-dimethoxy-4-hydroxymethylphenyl)-L-phenylalanine ethyl ester The compound in Example 1-(5) was also obtained by the following alternative route.

(1) N-(2,6-Dichlorobenzoyl)-L-tyrosine ethyl ester (171.4 g) was obtained in a similar manner as described in Example 1-(5) from L-tyrosine ethyl ester hydrochloride (110.0 g). mp. 141-142° C.; IR (Nujol) 3381, 3329, 1718, 1659 cm$^{-1}$; MS (APCI) m/z 382 (M+H).

(2) The product obtained above (130 q) was converted into N-(2,6-dichlorobenzoyl)-O-(trifluoromethanesulfonyl)-L-tyrosine ethyl ester (174.9 g) in a similar manner as described in Example 1-(2). IR (Neat) 1737, 1651 cm$^{-1}$; MS (APCI) m/z 514 (M+H).

(3) The product obtained above (174.9 g) was converted into the title compound (119.7 g) in a similar manner as described in Example 1-(3).

Reference Example 4

N-(2,6-Difluorobenzoyl)-4-(2,6-dimethoxy-4-hydroxymethylphenyl)-L-phenylalanine ethyl ester The compound in Example 10-(1) was also obtained by the following alternative route.

(1) L-Tyrosine ethyl ester hydrochloride (10.0 g) was acylated with 2,6-difluorobenzoyl chloride in a similar manner as described in Example 1-(5) to give N-(2,6-difluorobenzoyl)-L-tyrosine ethyl ester (13.2 g). mp. 149-150° C.; IR (Nujol) 3424, 3277, 1721, 1660, 1624 cm$^{-1}$; MS (APCI) m/z 350 (M+H).

(2) The product obtained above (12.18 g) was converted into N-(2,6-difluorobenzoyl)-O-(trifluoromethanesulfonyl)-L-tyrosine ethyl ester (16.0 g) in a similar manner as described in Example 1-(2). mp. 76-78° C.; IR (Nujol) 3290, 1739, 1657, 1625, 1539, 1502, 1467, 1423, 1249, 1214, 1140, 1009, 891, 793 cm$^{-1}$; MS (APCI) m/z 482 (M+H).

(3) The product obtained above (7.7 g) was reacted with 2,6-dimethoxy-4-hydroxymethylbenzene boronic acid in a similar manner as described in Example 1-(3) to give the title compound (7.6 g).

Reference Example 5

N-(2-Chloro-6-fluorobenzoyl)-4-(2,6-dimethoxy-4-hydroxymethylphenyl)-L-phenylalanine ethyl ester The title compound in Example 19-(1) was also obtained by the following alternative route.

(1) L-Tyrosine ethyl ester hydrochloride (102 g) was acylated in a similar manner as described in Example 19-(1) to give N-(2-chloro-6-fluorobenzoyl)-L-tyrosine ethyl ester (137.2 g). mp. 144-145° C.; IR (Nujol) 3425, 3260, 1720, 1659, 1615 cm$^{-1}$; MS (APCI) m/z 366 (M+H).

(2) The product obtained above (136.2 g) was converted into N-(2-chloro-6-fluorobenzoyl)-O-(trifluoromethanesulfonyl)-L-tyrosine ethyl ester (189.8 g) in a similar manner as described in Example 1-(2). IR (Neat) 3283, 1738, 1657, 1605 cm$^{-1}$; MS (APCI) m/z 498 (M+H).

(3) The product obtained above (189.8 g) was converted into the title compound (142.3 g) in a similar manner as described in Example 1-(3).

The invention claimed is:

1. A method for treating multiple sclerosis, comprising administering to said patient an effective amount of a compound of formula [I]:

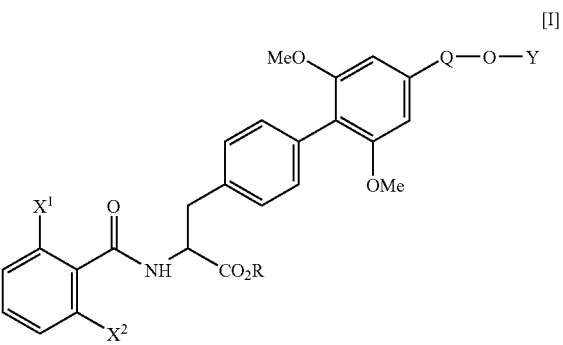

wherein X$^1$ is a halogen atom, X$^2$ is a halogen atom, Q is a —CH2— group or a —(CH$_2$)$_2$— group, Y is a C$_{1-6}$ alkyl group, CO$_2$R is a carboxyl group or a C$_{2-7}$ alkoxycarbonyl group, or a pharmaceutically acceptable salt thereof.

2. The method according to claim 1, wherein the compound is represented by the following formula [I-1]:

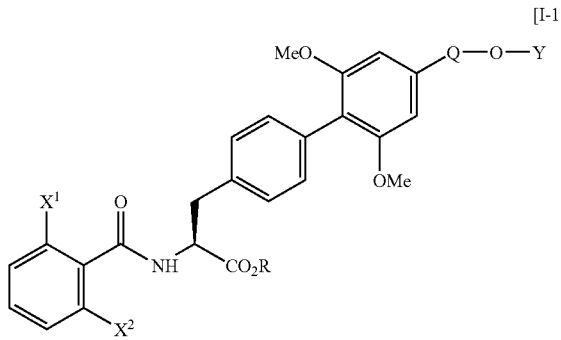

[I-1]

wherein the symbols are the same as defined in claim 1.

3. The method according to claim 2, wherein $X^1$ is chlorine atom or fluorine atom, $X^2$ is chlorine atom or fluorine atom, and Y is a $C_{1-4}$ alkyl group.

4. The method according to claim 3, wherein $X^1$ is chlorine atom or fluorine atom, $X^2$ is chlorine atom or fluorine atom, Q is a —$CH_2$— group, Y is methyl group, ethyl group, or n-propyl group, and $CO_2R$ is a carboxyl group, methoxycarbonyl group, ethoxycarbonyl group or tert-butoxycarbonyl group.

5. The method according to claim 3, wherein $X^1$ is fluorine atom, $X^2$ is chlorine atom or fluorine atom, Q is a —$CH_2$— group, and Y is methyl group or ethyl group.

6. The method according to claim 1, wherein the compound is selected from the group consisting of N-(2,6-di-fluorobenzoyl)-4-(2,6dimethoxy4-ethoxymethylphenyl)-L-phenylalanine, N-(2-chloro-6-fluorobenzoyl)-4-(2,6dimethoxy-4-ethoxymethylphenyl)-L-phenylalanine, N-(2chloro-6-fluorobenzoyl)-4-(2,6-dimethoxy-4-methoxymethylphenyl)-L-phenylalanine, and N-(2,6-difluorobenzoyl)-4-(2,6-dimethoxy-4-methoxymethylphenyl)-L-phenylalanine.

7. The method according to claim 1, wherein thc compound is N-(2,6-difluorobenzoyl)4-(2,6dimethoxy-4-ethoxymethylphenyl)-L-phenylalanine.

8. The method according to claim 1, wherein the compound is administered orally.

* * * * *